United States Patent
Ito et al.

(10) Patent No.: US 11,914,692 B2
(45) Date of Patent: Feb. 27, 2024

(54) INFORMATION PROCESSING APPARATUS AND INFORMATION PROCESSING METHOD

(71) Applicant: SONY CORPORATION, Tokyo (JP)

(72) Inventors: Atsushi Ito, Tokyo (JP); Takeshi Uemori, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 265 days.

(21) Appl. No.: 17/250,800

(22) PCT Filed: Oct. 28, 2019

(86) PCT No.: PCT/JP2019/042091
§ 371 (c)(1),
(2) Date: Mar. 4, 2021

(87) PCT Pub. No.: WO2020/095739
PCT Pub. Date: May 14, 2020

(65) Prior Publication Data
US 2021/0256280 A1 Aug. 19, 2021

(30) Foreign Application Priority Data
Nov. 6, 2018 (JP) .................................. 2018-209248

(51) Int. Cl.
*G06V 40/10* (2022.01)
*G06F 21/32* (2013.01)
(Continued)

(52) U.S. Cl.
CPC ................ *G06F 21/32* (2013.01); *G06T 7/74* (2017.01); *G06V 40/10* (2022.01); *G06V 40/11* (2022.01);
(Continued)

(58) Field of Classification Search
CPC .................. G01B 11/25; G03B 17/54; G06F 2203/04101; G06F 3/042; G06F 3/0425;
(Continued)

(56) References Cited

U.S. PATENT DOCUMENTS

| | | | | |
|---|---|---|---|---|
| 5,722,398 A | * | 3/1998 | Ishihara | ............... A61B 5/1455 600/322 |
| 7,966,060 B2 | * | 6/2011 | Smit | ...................... A61B 5/441 600/476 |

(Continued)

FOREIGN PATENT DOCUMENTS

| CN | 101317757 A | 12/2008 |
|---|---|---|
| CN | 102058393 A | 5/2011 |

(Continued)

OTHER PUBLICATIONS

Anderson, et al., "The optics of Human Skin", Journal of Investigative Dermatology, vol. 77, No. 1, Jul. 1981, pp. 13-19.

(Continued)

*Primary Examiner* — Ian L Lemieux
(74) *Attorney, Agent, or Firm* — CHIP LAW GROUP

(57) ABSTRACT

Provided is an information processing apparatus that includes an acquisition section that acquires a multi-spectral image consistent with an imaging result of a subject by using light divided into a plurality of wavelength bands and an extraction section that extracts a feature value by performing a computational process on the multi-spectral image on the basis of coefficients appropriate to absorption spectral properties of one or more pigments.

15 Claims, 15 Drawing Sheets

(51) Int. Cl.
*G06T 7/73* (2017.01)
*G06V 10/58* (2022.01)
*G06V 40/14* (2022.01)

(52) U.S. Cl.
CPC .... *G06T 2207/30101* (2013.01); *G06V 10/58* (2022.01); *G06V 40/14* (2022.01)

(58) Field of Classification Search
CPC ..... G06F 21/32; H04N 9/3129; A61B 5/1171; A61B 5/0077; A61B 5/02007; A61B 5/1128; A61B 5/117; A61B 5/489; A61B 5/7267; A61B 5/00; A61B 5/1455; G06T 2207/30088; G06T 2207/30101; G06T 7/74; G06T 1/00; G06V 10/58; G06V 40/14; G06V 40/10; G06V 40/11; G01N 21/27

See application file for complete search history.

(56) References Cited

U.S. PATENT DOCUMENTS

| | | | | |
|---|---|---|---|---|
| 9,597,033 | B2* | 3/2017 | Ohki | G06T 7/0012 |
| 2014/0016832 | A1 | 1/2014 | Kong et al. | |
| 2015/0356339 | A1* | 12/2015 | Demos | H04N 23/74 |
| | | | | 348/77 |
| 2016/0296119 | A1* | 10/2016 | Nakamura | A61B 5/0075 |
| 2017/0337412 | A1* | 11/2017 | Bhat | A61B 5/1172 |
| 2018/0137620 | A1* | 5/2018 | Gatto | G06V 40/40 |
| 2019/0025985 | A1 | 1/2019 | Yamauchi | |
| 2019/0080153 | A1* | 3/2019 | Kalscheur | G06V 40/166 |
| 2019/0133502 | A1* | 5/2019 | Gomi | A61B 5/14532 |
| 2020/0138360 | A1* | 5/2020 | Fan | A61B 5/02007 |
| 2021/0383571 | A1* | 12/2021 | Tomizawa | G01N 21/27 |

FOREIGN PATENT DOCUMENTS

| | | |
|---|---|---|
| CN | 108463793 A | 8/2018 |
| EP | 2649558 A1 | 10/2013 |
| JP | 2002-150296 A | 5/2002 |
| JP | 2005-300241 A | 10/2005 |
| JP | 2012228503 A | 11/2012 |
| JP | 2013-043017 A | 3/2013 |
| JP | 5377580 B2 | 12/2013 |
| JP | 2014233344 A | 12/2014 |
| JP | 2016-030095 A | 3/2016 |
| JP | 2017000742 A | 1/2017 |
| JP | 2017-126182 A | 7/2017 |
| JP | 2018008039 A | 1/2018 |
| JP | 2018023756 A | 2/2018 |
| JP | 2018089369 A | 6/2018 |
| WO | 2012/078114 A1 | 6/2012 |
| WO | 2017/122634 A1 | 7/2017 |

OTHER PUBLICATIONS

Weyrich, et al., "Analysis of Human Faces using a Measurement-Based Skin Reflectance Model", ACM Transactions on Graphics, vol. 25, No. 3, Jul. 2006, 12 pages.

Tseng, et al., "Chromophore Concentrations, Absorption and Scattering Properties of Human Skin in-vivo", Optics express, vol. 17, No. 17, PMC2754563, Aug. 17, 2009, pp. 14599-14617.

Masaki Watanabe, "Palm Vein Authentication", Advances in Biometrics, 2008, pp. 75-88.

Kanzawa, et al., "Human Skin Detection by Visible and Near-Infrared Imaging", MVA2011 IAPR Conference on Machine Vision Applications, Jun. 13-15, 2011, Nara, Japan, pp. 503-507.

Erik Haggblad, "In Vivo Diffuse Reflectance Spectroscopy of Human Tissue: From Point Measurements to Imaging", Linkoping Studies in Science and Technology, Dissertations, No. 1210, 2008, 100 pages.

International Search Report and Written Opinion of PCT Application No. PCT/JP2019/042091, dated Nov. 26, 2019, 10 pages of ISRWO.

Ohno, et al., "Estimation of Spectral Distribution Using Multi-Band Images and Its Application", IEEJ Transactions on Electronics Information and Systems, vol. 125, No. 5, Jan. 2005, pp. 792-799.

Hayato Ohno, "Spectral Characteristic Presumption by a Multi Band Image, Its Application", Journal of the Institute of Electrical Engineers of Japan C (an electron and an information system section magazine), Aug. 1, 2005, pp. 792-799, 125th vol. No. 5. pp. 792-799.

* cited by examiner

MULTI-SPECTRAL IMAGE
(CHANNEL IMAGE k)

EXAMPLE 1 OF EXTRACTION RESULT OF FEATURE VALUE

EXAMPLE 2 OF EXTRACTION RESULT OF FEATURE VALUE

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2019/042091 filed on Oct. 28, 2019, which claims priority benefit of Japanese Patent Application No. JP 2018-209248 filed in the Japan Patent Office on Nov. 6, 2018. Each of the above-referenced applications is hereby incorporated herein by reference in its entirety.

TECHNICAL FIELD

The present disclosure relates to an information processing apparatus, an information processing method, and a program.

BACKGROUND ART

With the advance of image processing techniques, there have been proposed a variety of recognition techniques using a captured image including one by which a subject in an image captured by an imaging section such as a digital camera (in other words, an image sensor) is recognized by analyzing the captured image, one by which a surrounding environment of the imaging section is recognized, and the like. Also, recent years have witnessed the proposal of wide-ranging techniques that allow for use of an image consistent with an imaging result of a given subject for user identification or authentication by applying the image analysis techniques (e.g., recognition technique) as described above. For example, PTL 1 discloses an example of a technique for extracting a vein pattern by analyzing an image of the back of a user's hand and using the vein pattern in question to authenticate the user in question.

CITATION LIST

Patent Literature

[PTL 1]
Japanese Patent No. 5377580

SUMMARY

Technical Problem

Meanwhile, information extracted on the basis of an analysis result of a captured image (e.g., information used for identification of a given target) may, at least partially, change depending on the time due to an external factor (disturbance) such as changes in the state of the subject and the image capture environment (i.e., surrounding environment at the time when the image is captured). In other words, it may be difficult to ensure the identity of information regarding the subject extracted from the captured image depending on circumstances at the time. As a result, for example, under the circumstances where a given target is identified on the basis of information regarding a subject extracted from a captured image, an impact of the external factor described above may manifest itself in the captured image, thus resulting in reduced accuracy and reliability of identification of the target and leading, by extension, to difficulty in identification the target.

In light of the foregoing, the present disclosure proposes a technique that allows for extraction of information inherent to a subject from a captured image in a more suitable manner, irrespective of the change in circumstances at the time when the image is capture.

Solution to Problem

According to the present disclosure, there is provided an information processing apparatus including an acquisition section adapted to acquire a multi-spectral image consistent with an imaging result of a subject by using light divided into a plurality of wavelength bands and an extraction section adapted to extract a feature value by carrying out a computational process on the multi-spectral image on the basis of coefficients appropriate to absorption spectral properties of one or more pigments.

Also, according to the present disclosure, there is provided an information processing method by a computer including acquiring a multi-spectral image consistent with an imaging result of a subject by using light divided into a plurality of wavelength bands and extracting a feature value by carrying out a computational process on the multi-spectral image on the basis of coefficients appropriate to absorption spectral properties of one or more pigments.

Also, according to the present disclosure, there is provided A program causing a computer to execute acquiring a multi-spectral image consistent with an imaging result of a subject by using light divided into a plurality of wavelength bands and extracting a feature value by carrying out a computational process on the multi-spectral image on the basis of coefficients appropriate to absorption spectral properties of one or more pigments.

DESCRIPTION OF EMBODIMENTS

Preferred embodiments of the present disclosure will be described below with reference to attached drawings. It should be noted that, in the present specification and the drawings, constituent elements having substantially the same functional configuration will be denoted by the same reference signs to omit redundant description.

Figure 1:
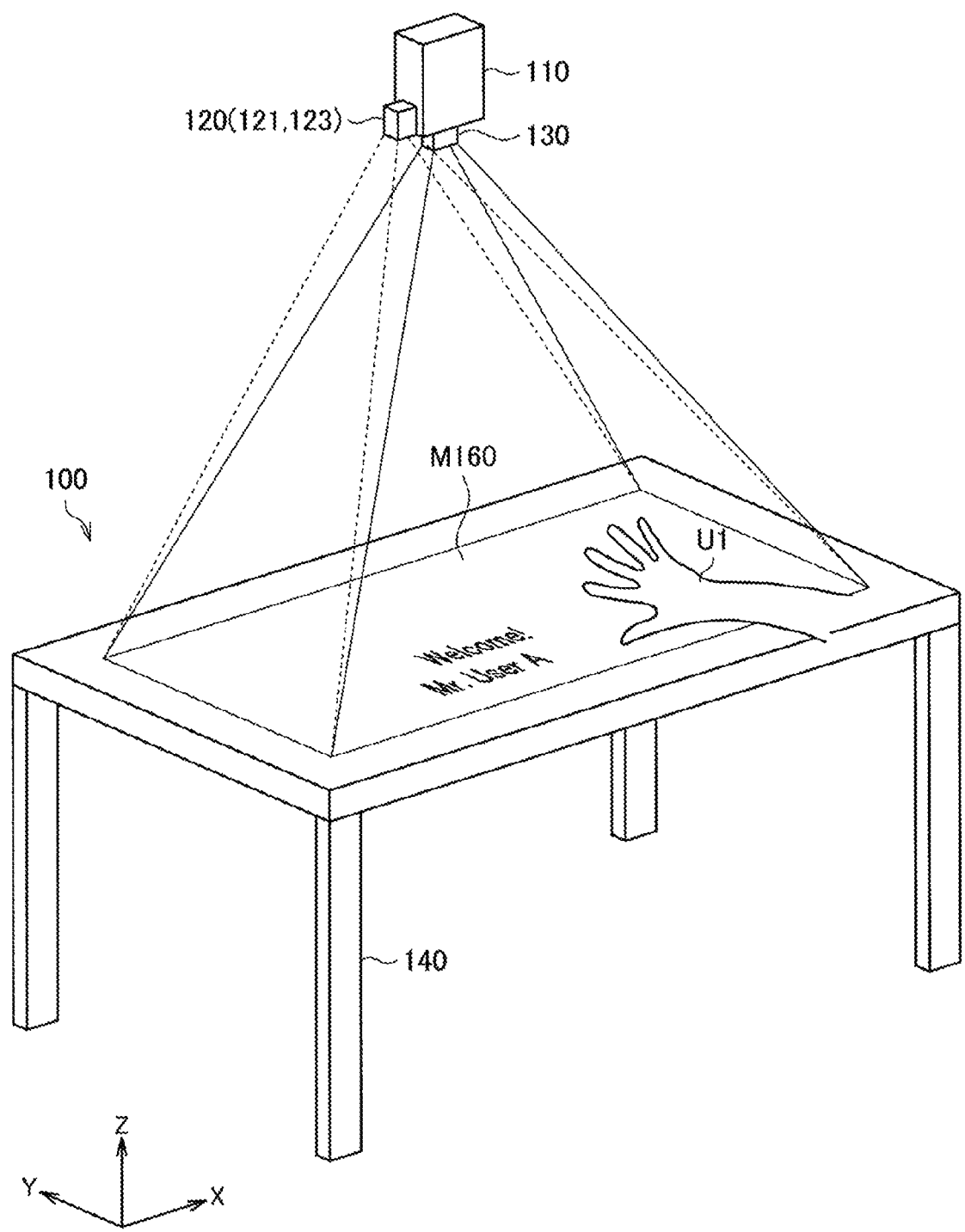
FIG. 1 is an explanatory diagram for describing an example of a schematic configuration of an apparatus to which a technique according to an embodiment of the present disclosure is applied.

The description will be given in the following order.
1. Schematic Configuration
2. Technical Problems
3. Technical Properties
3.1 Basic Concept
3.2 First Embodiment
3.2.1. Functional Configuration
3.2.2. Processes
3.2.3. Specific Examples of Feature Values
3.3. Second Embodiment
3.3.1. Functional Configuration
3.3.2. Details of Feature Value
3.3.3. Working Example
3.4. Third Embodiment
3.4.1. Schematic Configuration
3.4.2. Functional Configuration
3.4.3. Example of Controlling Light Irradiated from Light Source
4. Hardware Configuration
5. Conclusion 1. Schematic Configuration A description will be given first of an example of a schematic configuration of an apparatus to which a technique according to an embodiment of the present disclosure is applied. FIG. 1 is an explanatory diagram for describing an example of a schematic configuration of an apparatus to which a technique according to an embodiment of the present disclosure is applied, illustrating an example of a configuration of a display apparatus for presenting information by projecting video onto a given projection plane.

As illustrated in FIG. 1, a display apparatus 100 includes a sensor box 120, an output section 130 for presenting display information, and a main body 110 having a control section for controlling a variety of actions of the display apparatus 100.

The display apparatus 100 is installed, for example, above a table 140 or the like to face a top side of the table 140 in question. The display apparatus 100 causes the output section 130 to project display information onto the top side of the table 140 as a projection plane, presenting the display information to a user and accepting operations from the user using the display apparatus 100 in response to the projected display information. It should be noted that a reference sign M160 represents a region (i.e., projection plane) onto which information output from the output section 130 (i.e., display information) is projected.

Also, the sensor box 120 has a detection section 121 that detects various types of information like what is generally called a sensor. The detection section 121 recognizes details of operations of the user using the display apparatus 100, shapes and patterns of objects resting on the table 140, and the like. In the example illustrated in FIG. 1, for example, the detection section 121 is installed such that a detection range is formed to span from above the table 140 toward the top side of the table 140. That is, the detection section 121 is isolated from the table 140 on which information is displayed.

As a specific example, the detection section 121 can include what is generally called a distance measurement sensor. Also, as another example, the detection section 121 may include, for example, a camera that images the table 140 with a single imaging optical system (e.g., a series of lens groups) or a stereo camera capable of recording information in a depth direction by imaging the table 140 with a plurality of imaging optical system (e.g., two imaging optical systems). It should be noted that the present description is given assuming that the detection section 121 is configured as what is generally called a stereo camera.

In a case where a stereo camera is used as the detection section 121, a visible light camera, an infrared camera, or the like is applicable, for example, as the stereo camera. The use of a stereo camera as the detection section 121 allows for acquisition of depth information by the detection section 121. As a result of acquisition of depth information by the detection section 121, the display apparatus 100 can detect a real object such as a hand or an object lying on the table 140. Also, as a result of acquisition of depth information by the detection section 121, the display apparatus 100 can detect contact or proximity of an operating body such as a user's hand to the table 140 or detachment of the operating body from the table 140.

Such a configuration allows for the display apparatus 100 to recognize, in response to display information projected onto the region M160 on the top side of the table 140, an operation made by the operating body such as a user's hand and carry out various functions in accordance with details of the operation in question.

Also, the sensor box 120 has an imaging section 123 for capturing an image of the region M160 on the top side of the table 140. The display apparatus 100 illustrated in FIG. 1 performs analysis of the image captured by the imaging section 123 in question, thus recognizing a subject captured in the image and performing various processing tasks by using the recognition result. As a specific example, the display apparatus 100 may extract, from within the image consistent with the imaging result of the imaging section 123, a user's hand U1 captured as a subject, and identify or authenticate the user in question on the basis of the image of the hand U1 in question. It should be noted that image analysis described above and various processing tasks based on the result of the image analysis in question may be controlled by the control section provided in the main body 110. Also, the imaging section 123 may play the role of the detection section 121. That is, the operation made by the operating body such as a user's hand may be recognized in accordance with the result of the image analysis consistent with the imaging result of the imaging section 123. In this case, the detection section 121 may not be provided separately.

It should be noted that the above configuration of the display apparatus 100 is merely an example and that the configuration of the display apparatus 100 is not necessarily limited to the example illustrated in FIG. 1 as long as each of the above functions can be realized. As a specific example, a control section for controlling the actions of the sensor box 120 and the output section 130 may be provided in an apparatus different from the display apparatus 100. In this case, the control section in question may control the actions of the sensor box 120 and the output section 130 on the basis of communication with the display apparatus 100 via a network (e.g., the main body 110). Also, the sensor box 120, the output section 130, and the main body 110 may not be configured integrally with each other. As a specific example, either of the sensor box 120 or the output section 130 may be provided in another apparatus connected to the main body 110 via a network. That is, the display apparatus 100 illustrated in FIG. 1 may be configured as a system a plurality of whose apparatuses connected via a network work in cooperation.

A schematic configuration of an apparatus to which a technique according to an embodiment of the present disclosure is applied has been described above with reference to FIG. 1.

2. Technical Problems

Next, a description will be given bellow of technical problems of the information processing apparatus (or the information processing system) according to an embodiment of the present disclosure. Specifically, an example of user identification and authentication using an analysis result of a captured image will be outlined first, followed by outlining of technical problems associated with extraction, from a captured image, of user-inherent information that can be used for identification or authentication of the user.

A technique referred to as what is generally called vein authentication is an example of a technique for achieving user identification or authentication by using an image captured by an imaging section such as a digital camera (in other words, image sensor). For example, Japanese Patent No. 5377580 discloses an example of a technique regarding vein authentication. For example, vein authentication performs image analysis on an image consistent with an imaging result of the back of a user's hand by using light in the infrared band (e.g., infrared image), thus extracting a distinctive portion of a vein pattern such as a vein line curve or a branch as a feature value and carrying out user identification or authentication on the basis of the feature value in question. Because of such a property, vein authentication excels in terms of difficulty in counterfeiting information used for authentication and resistance to change of information used for authentication over time.

Meanwhile, vein authentication tends to require relatively high resolution for vein pattern sensing. In other words, vein authentication may decline in accuracy and reliability associated with user recognition or authentication due to insufficiency of the captured image resolution, resulting, by extension, in difficulty with the identification in question or the authentication in question. Accordingly, for example, under the circumstances where information used for authentication (e.g., user's hand) is to be detected over a relatively wide region like the table 140, a device offering higher resolution is required as an imaging section proportionally with a breadth of the region. Also, vein authentication tends to be affected by the change in posture of the user's hand (and, by extension, vein pattern). As a result, for example, if the hand is tilted significantly relative to the imaging section, the accuracy and the reliability of user identification or authentication may decline. Accordingly, in a case of realizing vein authentication-based user identification or authentication in the display apparatus 100 illustrated in FIG. 1, a troublesome operation such as holding the hand in a given posture to permit detection of a vein pattern is possibly required during user identification or authentication.

Also, there can be cited, as another example, a technique in which the user makes a series of gestures using a given part of his or her body (e.g., rock, paper, and scissors gestures using a hand) and the imaging result of the gestures in question is checked against the imaging result of the gestures made by the user in question imaged in advance, thus achieving the user identification or authentication in question. An example of the technique is disclosed, for example, in Japanese Patent Laid-open No. 2002-150296. However, even in a case where the technique in question is used, a troublesome operation such as that of making the above series of gestures is required.

Also, there can be cited, as still another example, a technique in which near-infrared absorption spectra are measured for user's hair and criteria acquired by performing a given statistical process on spectral data consistent with the result of the measurement in question are used, thus achieving user identification or authentication. An example of the technique is disclosed, for example, in Japanese Patent Laid-open No. 2005-300241. However, in a case where information is extracted from a region such as user's hand that stretches two-dimensionally as in the example illustrated in FIG. 1, reflection spectra fluctuate spatially, possibly making it difficult to ensure identity of extracted information. Specifically, if a portion of the user's hand used for identification or authentication becomes misaligned, different information may be extracted. Because of such a property, an operation such as holding the hand in a given posture for a certain amount of time is required to prevent misalignment of the region from which to extract information, possibly resulting in a relatively significant physical constraint that puts a strain on the user.

As described above, information (e.g., information used for identification of a given target) extracted on the basis of an analysis result of a captured image may change at least partially depending on the time due to an external factor (disturbance) such as the change in the state of the subject and the image capture environment (i.e., surrounding environment at the time of image capture). That is, between a plurality of different captured images of the same target as a subject, the identity of the information regarding the subject in question (e.g., information regarding properties inherent to the subject) extracted from each of the plurality of captured images is not necessarily ensured depending on the circumstances at the time. In such a case, for example, under the circumstances where a given target (e.g., user) is identified on the basis of information of the subject extracted from captured images as in each example described above, the impact of the external factor may possibly manifest itself in the captured image, thus resulting in reduced accuracy and reliability of the identification of the target and leading, by extension, to difficulty in identification of the target. In other words, it may be difficult to ensure the identity of information of a subject extracted from captured images depending on the circumstances at the time.

In light of the circumstances described above, an information processing apparatus (or an information processing system) according to an embodiment of the present disclosure proposes a technique that realizes the identification or authentication of the user in question using captured images of a user's body region such as a hand as a subject through a simpler operation. In other words, the present disclosure proposes a technique that allows for extraction of information inherent to a subject from a captured image in a more suitable manner, irrespective of the change in circumstances at the time of image capture.

3. Technical Properties

A description will be given next of technical properties of an information processing system according to an embodiment of the present disclosure. It should be noted that, for more ease of understanding of the description, technical properties of the information processing system according to the present embodiment will be described with focus on a case of identification or authentication of a user on the basis of a captured image of a given body region (e.g., user's hand) of the user in question as a subject. Specifically, technical properties of the information processing system according to the present embodiment will be described with focus on a case where, of information regarding a user's skin (hereinafter also referred to as "skin information"), information inherent to the user is extracted, as a feature value, from a captured image of the user's skin as a subject and where the feature value is used for user identification or authentication.

<3.1. Basic Concept>

Examples of properties of skin information will be outlined first, followed by outlining of a basic concept of the technique by which the information processing system according to an embodiment of the present disclosure extracts skin information from a captured image as information inherent to a user for identification or authentication of the user in question.

For example, according to an optical skin model proposed in Literature 1 listed below, it is known that, in a normal skin, the skin color is determined, with the exception of surface reflection of approximately 5% of incident light and diffuse reflection of approximately 10% thereof, by scattering in a dermis and absorption of light by melanin in an epidermis and blood in a vascular plexus immediately under the epidermis. Literature 1: R. R. Anderson, J. A. Parrish, "The optics of Human Skin," The Journal of Investigative Dermatology, Vol. 77, pp. 13-19, 1981.

Also, Literature 2 listed below discloses a measurement result, by an optical device, of diffuse subsurface scattering properties of the face skin for 149 people having different ages, sexes, and skin types. According to this measurement result, it is known that absorption and scattering spectral properties in subsurface scattering of the skin surface vary from one individual to another (i.e., depending on the age, the sex, and the skin type).

Literature 2: T. Weyrich, W. Matusik, H. Pfister, B. Bickel, C. Donner, C. Tu, J. McAndless, J. Lee, A. Ngan, H. W. Jensen, and M. Gross, "Analysis of human faces using a measurement-based skin reflectance model," ACM Trans. On Graphics (Proc. SIGGRAPH 2006), vol. 25, no. 3, pp. 1013-1024, 2006.

Also, Literature 3 listed below describes a method for measuring optical spectral properties of skin for 18 people having different skin types and for estimating concentrations of skin pigments such as oxidized hemoglobin, deoxidized hemoglobin, and melanin from measured values. The literature in question also states that optical spectral properties (or pigment concentrations) of skin vary from one individual to another.

Literature 3: Sheng-Hao Tseng, Paulo Bargo, Anthony Durkin, and Nikiforos Kollias, "Chromophore concentrations, absorption and scattering properties of human skin in-vivo," Opt. Express 17, 14599-14617 (2009)

Also, Literature 4 listed below discloses an example of using an absorption property of deoxidized hemoglobin at a wavelength of 760 nm in vein authentication using a near-infrared image of a palm. At the wavelength in question, light is not scattered or reflected much. Accordingly, by acquiring a vein pattern image with light at the wavelength in question, for example, it is possible to acquire a two-dimensional image with suppressed light intensity (i.e., two-dimensional image with lower intensity) in a region where the light at the wavelength in question is absorbed (i.e., region where deoxidized hemoglobin is distributed).

Literature 4: Masaki Watanabe, "Palm vein authentication," Advances in Biometrics pp 75-88, 2008

In view of the above, the skin color is primarily determined by scattering of light in the dermis and absorption of light by melanin in the epidermis and blood in the vascular plexus immediately under the epidermis, and absorption and scattering spectral properties under the skin surface can be a unique feature value for identifying an individual.

Accordingly, the present disclosure proposes a technique that allows for extraction of information inherent to a user (feature value) that can be used for identification or authentication of the user in question from a captured image of a skin by using spectral properties (absorption spectral properties, in particular) of the user's skin pigments (e.g., melanin and hemoglobin).

Specifically, the information processing system according to an embodiment of the present disclosure, like a what is generally called a multi-spectral camera, extracts, as information inherent to a user (i.e., information that can be used for identification or authentication of the user in question), a feature value having spectral properties of the user's skin reflected therein by using an imaging apparatus (hereinafter also referred to as "spectral measurement apparatus") capable of capturing an image of a subject (what is generally called a multi-spectral image) with light divided into a plurality of wavelength bands. More specifically, an analytic process appropriate to the absorption spectral property of a pigment included in the skin color such as melanin or hemoglobin is performed on a multi-spectral image (hereinafter referred to as a "two-dimensional spectral data") of a skin region captured with a spectral apparatus, thus extracting information inherent to the user in question (feature value) that allows for realization of user identification or authentication with higher accuracy.

For example, hemoglobin is present in blood. Accordingly, in a case where attention is focused on some positions of the skin region, the concentration of hemoglobin in question changes from one moment to another, causing the skin color to change from one moment to another. In such a case, for example, a process of suppressing (e.g., canceling) the impact of hemoglobin in question on two-dimensional spectral data of skin acquired by the spectral measurement apparatus may be performed by using a known absorption spectral property of hemoglobin, thus extracting a feature value. A relationship between such a feature value as machine learning input data and the user is learnt by a recognizer, and the recognizer is used for user identification or authentication by using a captured skin image, thus making it possible to realize more accurate personal recognition in a manner robust to a change in hemoglobin concentration.

Also, melanin may grow in concentration due to sunburn or the like, causing the skin color to change as a result. In such a case, a process of suppressing (e.g., canceling) the impact of melanin in question on two-dimensional spectral data of skin acquired by the spectral measurement apparatus may be performed by using a known absorption spectral property of melanin, thus extracting a feature value. The relationship between such a feature value as machine learning input data and the user is learnt by a recognizer, and the recognizer is used for user identification or authentication by using a captured skin image, thus making it possible to realize more accurate personal recognition in a manner robust to the change in the skin color due to sunburn.

Also, because of the properties described above, the technique according to the present disclosure does not always require that the shape of the body region such as a hand be observable, thus making it possible to identify an individual even under the circumstances where only part of the skin is observable.

The basic concept of the technique has been outlined above by which the information processing system according to an embodiment of the present disclosure extracts skin information from a captured image as information inherent to a user for identification or authentication of the user in question.

<3.2. First Embodiment>

Next, as a first embodiment of the present disclosure, a description will be given of an example of an information processing system that extracts information inherent to a user (feature value) from a skin image captured by an imaging section (spectral measurement apparatus) capable of capturing a multi-spectral image and performs user recognition or authentication.

<3.2.1. Functional Configuration>

Figure 2:
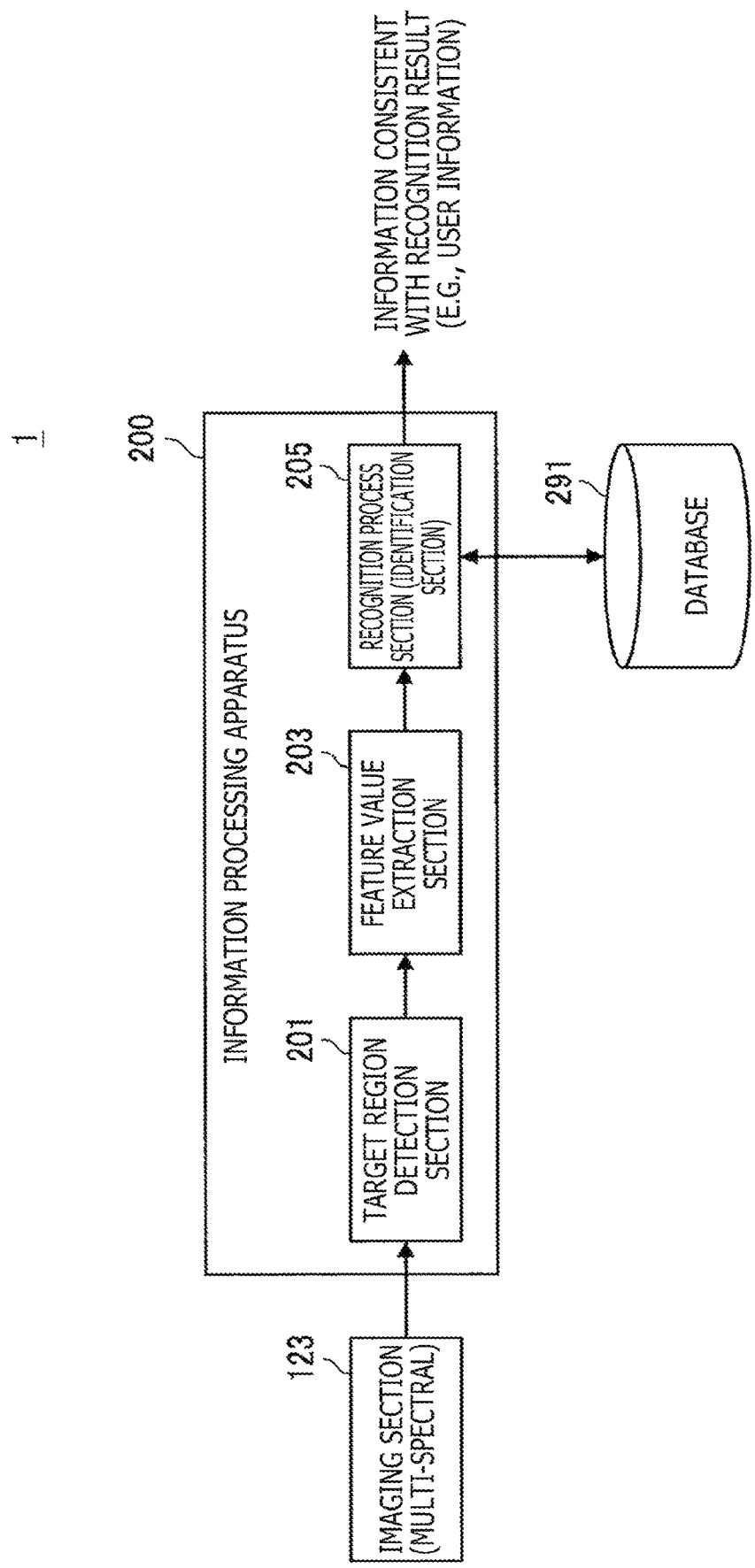
FIG. 2 is a block diagram illustrating an example of a functional configuration of an information processing system according to a first embodiment of the present disclosure.

A description will be given first of an example of a functional configuration of the information processing system according to the present embodiment with reference to FIG. 2. FIG. 2 is a block diagram illustrating an example of a functional configuration of the information processing system according to the present embodiment.

As illustrated in FIG. 2, an information processing system 1 according to the present embodiment includes the imaging section 123, an information processing apparatus 200, and a database 291.

The imaging section 123 is capable of capturing a multi-spectral image (in other words, two-dimensional spectral data) of a subject. For example, the imaging section 123 can be configured as a multi-spectral camera. Also, the imaging section 123 can correspond to the imaging section 123 provided in the sensor box 120 in the display apparatus 100 illustrated in FIG. 1. The imaging section 123 outputs a multi-spectral image consistent with an imaging result of the subject (e.g., given body region of the user) to the information processing apparatus 200.

The information processing apparatus 200 includes a target region detection section 201, a feature value extraction section 203, and a recognition process section 205. The information processing apparatus 200 can be included, for example, as at least part of the main body 110 in the display apparatus 100 illustrated in FIG. 1.

The target region detection section 201 acquires a multi-spectral image consistent with an imaging result of the subject from the imaging section 123 and performs a given analytic process (e.g., image analysis) on the multi-spectral image, thus detecting (extracting) a target region satisfying a given condition from the multi-spectral image. As a specific example, the target region detection section 201 performs image analysis on the multi-spectral image, thus detecting a region corresponding to the user's skin (hereinafter also referred to as a "skin region") from the multi-spectral image. It should be noted that, as long as a skin region can be detected (extracted) from a multi-spectral image, the method for doing so is not particularly limited and that an existing approach may be used. As a specific example, a region representing the skin color may be detected by converting spectroscopic data into an HSV color space and performing a threshold process on the conversion result in question. Also, under a condition where the camera is kept at the same position and in the same posture, a skin region may be detected by using differential background information.

Also, Literature 5 listed below discloses an example of a technique of extracting a skin region with more accuracy. The same technique acquires data regarding two bands, one with a center wavelength of 870 nm and another with a center wavelength of 970 nm, thus extracting a skin region from the difference therebetween. Also, the same literature discloses a technique of further acquiring data regarding a band with a center wavelength of 1050 nm and extracting a skin region more elaborately on the basis of a set intersection between the difference between 870 nm data and 970 nm data and the difference between 970 nm data and 1050 nm data.

Literature 5: Kanazawa et al "Human Skin Detection by Visible and Near-Infrared Imaging," MVA2011 IAPR Conference on Machine Vision Applications, Jun. 13-15, 2011

Figure 4:
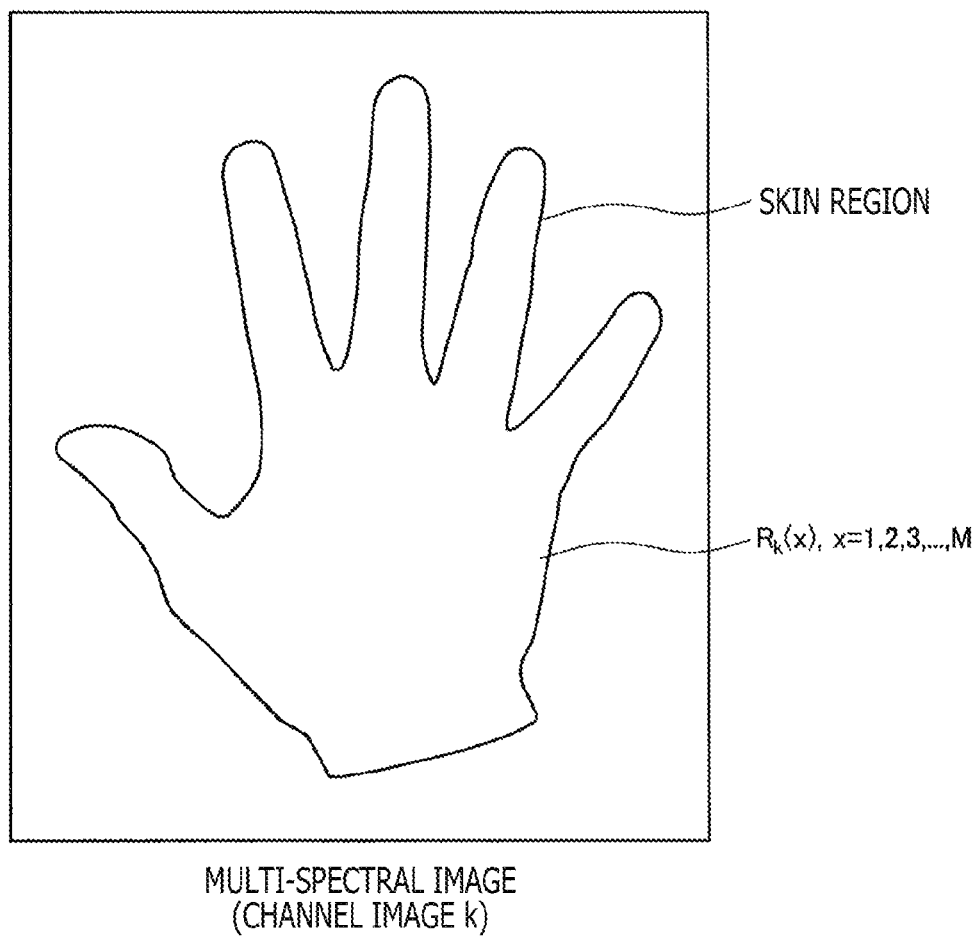
FIG. 4 is a diagram illustrating an example of a detection result of a skin region.

For example, FIG. 4 is a diagram illustrating an example of a detection result of a skin region. Specifically, the example illustrated in FIG. 4 depicts an example of a case where a skin region is detected from a multi-spectral image of the user's hand as a subject. In FIG. 4, $R_k(x)$ represents the pixel value (i.e., detection result of a spectroscopic component of channel k) at a position "x" in a multi-spectral image in a case where the wavelength band (channel) from which information is acquired as a multi-spectral image is "k."

As described above, the target region detection section 201 detects a target region (e.g., skin region) satisfying a given condition from the acquired multi-spectral image and outputs information regarding the target region in question to the feature value extraction section 203.

The feature value extraction section 203 acquires, from the target region detection section 201, information regarding a target region (e.g., skin region) detected from a multi-spectral image consistent with an imaging result of the imaging section 123. The feature value extraction section 203 performs, on the target region detected from the multi-spectral image, an analytic process appropriate to a spectral property of a given pigment, thus extracting a feature value. As a specific example, the feature value extraction section 203 may extract a feature value by performing, on the skin region (i.e., target region) detected from the multi-spectral image, an analytic process appropriate to the absorption spectral property of a skin pigment such as melanin or hemoglobin. It should be noted that a specific example of a feature value extracted by an analytic process appropriate to the absorption spectral properties of skin pigments for a skin region will be described separately later together with details of the extraction method of the feature value in question (i.e., details of the analytic process).

As described above, the feature value extraction section 203 extracts a feature value from a target region detected from the multi-spectral image, outputting information regarding the feature value to the recognition process section 205.

The recognition process section 205 acquires information regarding a feature value from the feature value extraction section 203, performing processes associated with recognition, identification, authentication, and the like of a given target on the basis of the feature value in question. As a specific example, the recognition process section 205 may carry out user identification or authentication on the basis of a feature value extracted from a skin region.

Also, the recognition process section 205 may perform processes associated with recognition, identification, authentication, and the like of a given target on the basis of the feature value by using a recognizer that has undergone machine learning taking the feature value in question as input. In this case, the recognition process section 205 may check the feature value acquired from the feature value extraction section 203 against data stored in advance in a given storage region (e.g., database 291) (i.e., data based on the feature value previously acquired), thus carrying out recognition, identification, authentication and the like of a given target. As a specific example, the recognition process section 205 may check the feature value acquired from the feature value extraction section 203 against data stored on a user-by-user basis in advance in the storage region (i.e., data consistent with learning results of machine learning), thus identifying to which user the skin captured in the multi-spectral image belongs. This allows the recognition process section 205 to carry out user identification or authentication on the basis of the acquired feature value.

Then, the recognition process section 205 outputs, to a given output destination, information consistent with processing results associated with recognition, identification, authentication, and the like of a given target based on the acquired feature value. As a specific example, the recognition process section 205 may output, to a given output destination, information regarding a user (e.g., user ID) in accordance with results of the user identification or authentication based on the feature value extracted from the skin region.

The database 291 temporarily or permanently stores a variety of pieces of data in a readable manner. As a specific example, the database 291 may store data consistent with results of machine learning taking the previously acquired feature value as input data (in other words, data to be checked against the newly acquired feature value).

It should be noted that the configuration described above is merely an example and that the configuration of the information processing system 1 is not limited to the example illustrated in FIG. 2. As a specific example, at least any one of the imaging section 123 and the database 291 may be configured integrally with the information processing apparatus 200. Also, as another example, some functions of the information processing apparatus 200 may be provided externally to the information processing apparatus 200 in question. As a specific example, a portion corresponding to the recognition process section 205 may be provided externally to the information processing apparatus 200. Also, at least some functions of the information processing apparatus 200 may be realized by actions in cooperation of a plurality of apparatuses. It should be noted that, of the information processing apparatus 200, the portion that acquires a multi-spectral image from which a feature value is extracted (e.g., multi-spectral image consistent with imaging results of the imaging section 123) corresponds to an example of an "acquisition section."

An example of a functional configuration of the information processing system according to the present embodiment has been described above with reference to FIG. 2.

<3.2.2. Processes>

Figure 3:
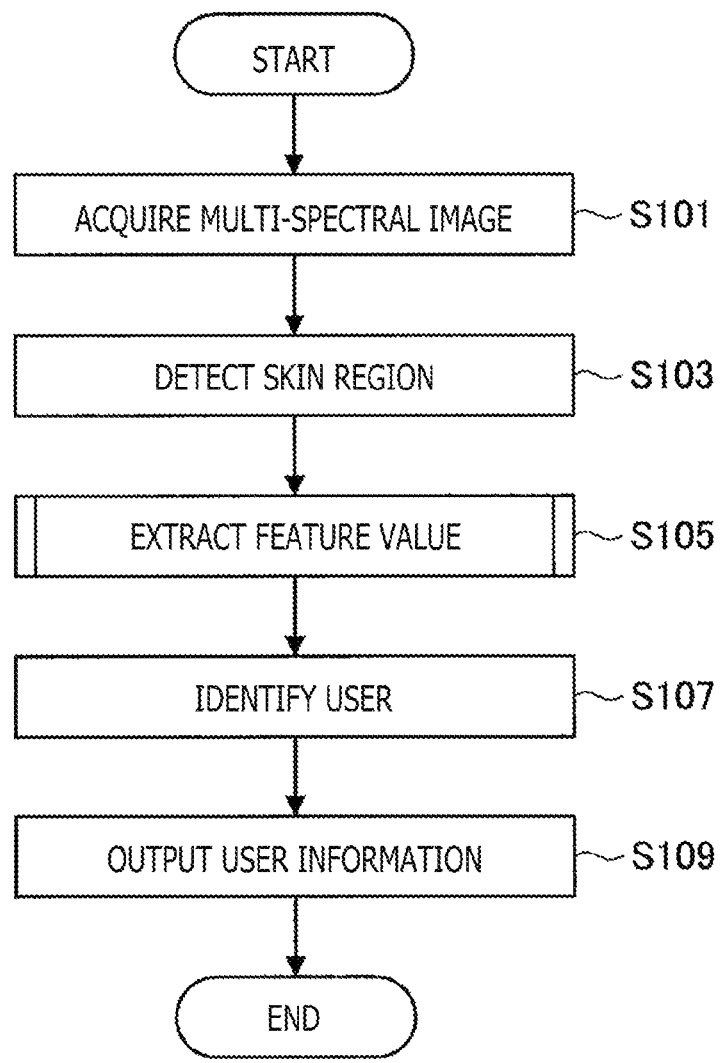
FIG. 3 is a flowchart illustrating an example of a flow of a series of processes handled by the information processing system according to the first embodiment.

A description will be given next of an example of a flow of a series of processes handled by the information processing system according to the present embodiment with reference to FIG. 3. FIG. 3 is a flowchart illustrating an example of a flow of a series of processes handled by the information processing system according to the present embodiment. It should be noted that a case will be described of extraction of a feature value inherent to a skin on the basis of an imaging result of a multi-spectral image of the skin by an imaging section configured as a multi-spectral camera for identification of the user on the basis of the feature value in question.

As illustrated in FIG. 3, the information processing apparatus 200 acquires a multi-spectral image consistent with an imaging result of a subject from the imaging section 123 (S101). The information processing apparatus 200 (target region detection section 201) performs image analysis on the acquired multi-spectral image, thus detecting a skin region from the multi-spectral image (S103).

Next, the information processing apparatus 200 (feature value extraction section 203) performs, on the skin region detected from the multi-spectral image, an analytic process appropriate to a spectral property of a given skin pigment (e.g., melanin or hemoglobin), thus detecting a feature value (S105). It should be noted that details of the feature value in question will be described separately later together with the extraction method.

Next, the information processing apparatus 200 (recognition process section 205) checks the feature value extracted from the multi-spectral image against the data stored in advance in a given storage region (e.g., database 291), thus carrying out user identification or authentication (S107). Then, the information processing apparatus 200 (recognition process section 205) outputs, to a given output destination, information regarding the user in question (e.g., user ID) in accordance with the user identification or authentication result (S109).

An example of a flow of a series of processes handled by the information processing system according to the present embodiment has been described above with reference to FIG. 3.

<3.2.3. Specific Examples of Feature Values>

A description will be given next of a specific example of a feature value extracted by the information processing system according to the present embodiment of the present disclosure from a multi-spectral image consistent with an imaging result of a subject. It should be noted that, in the present description, an example of a feature value extracted, in accordance with an absorption spectral property of a skin pigment, from a captured image of a user's skin as a subject, in particular, will be explained together with details of the extraction method.

(First Candidate Feature Value)

A description will be given first, as a first candidate feature value, of an example of information distinctive to a subject (i.e., captured skin) extracted as a result of suppression of the impact of some skin pigments that has manifested itself within a multi-spectral image, together with the extraction method thereof.

For example, Literature 6 listed below discloses that, under the skin surface, oxidized hemoglobin, deoxidized hemoglobin, and melanin are primary pigments absorbing light and that absorbance of the skin attributable to these pigments can be modelled by using the Beer-Lambert law. It should be noted that, in the description given below, oxidized hemoglobin and deoxidized hemoglobin may be treated as a single hemoglobin for ease of understanding. That is, in a case where simply the remark "hemoglobin" is entered, we assume that both oxidized hemoglobin and deoxidized hemoglobin can be included unless otherwise specified.

Literature 6: ERIK HAGGBLAD, "IN VIVO DIFFUSE REFLECTANCE SPECTROSCOPY OF HUMAN TISSUE FROM POINT MEASUREMENTS TO IMAGIN," 2008

By using the Beer-Lambert law, it is possible to represent the absorbance attributable to melanin and hemoglobin at a wavelength $\lambda$ and at a spatial position x with the relational expression given below as (Expression 1).

[Math. 1]

$$A(x,\lambda)=C\_M(x)*A\_M(\lambda)+C\_H(x)*A\_H(\lambda)+O(x,\lambda) \quad \text{(Expression 1)}$$

In the above Expression 1, C_M(x) and C_H(x) represent concentrations of melanin and hemoglobin at the spatial position x, respectively. Also, A_M($\lambda$) and A_H($\lambda$) represent absorbance coefficients of melanin and hemoglobin at the wavelength $\lambda$, respectively. It should be noted that respective properties of the absorbance coefficients of melanin and hemoglobin are disclosed, for example, in the above Literature 3. Also, O(x,$\lambda$) represents an offset term that factors in the impact attributable to absorption and scattering by pigments other than melanin and hemoglobin.

Also, letting the measured value (e.g., pixel value of a multi-spectral image) acquired by a spectral measurement apparatus (e.g., multi-spectral camera) be denoted as P(x,$\lambda$), the apparent absorbance is represented by the relational expression given below as (Expression 2).

[Math. 2]

$$A(x,\lambda)=-\log 10(P(x,\lambda)) \quad \text{(Expression 2)}$$

Accordingly, on the basis of (Expression 1) and (Expression 2), the relationship between the measured spectral value and the pigment concentrations of melanin and hemoglobin, is represented by the relational expression given below as (Expression 3).

[Math. 3]

$$-\log 10(P(x,\lambda))=C\_M(x)*A\_M(\lambda)+C\_H(x)*A\_H(\lambda)+O(x,\lambda) \quad \text{(Expression 3)}$$

From the above (Expression 3), it is understood that individual differences (i.e., differences in skin color unevenness between individuals) occur due to differences in spatial distribution of melanin and hemoglobin concentrations (C_M(x) and C_H(x)). However, hemoglobin is present in blood, causing its concentration distribution to change from moment to moment. As a result, in a case where inherent information is extracted that can be used for personal recognition or identification from a captured skin image, hemoglobin may translate into noise.

Figure 5:
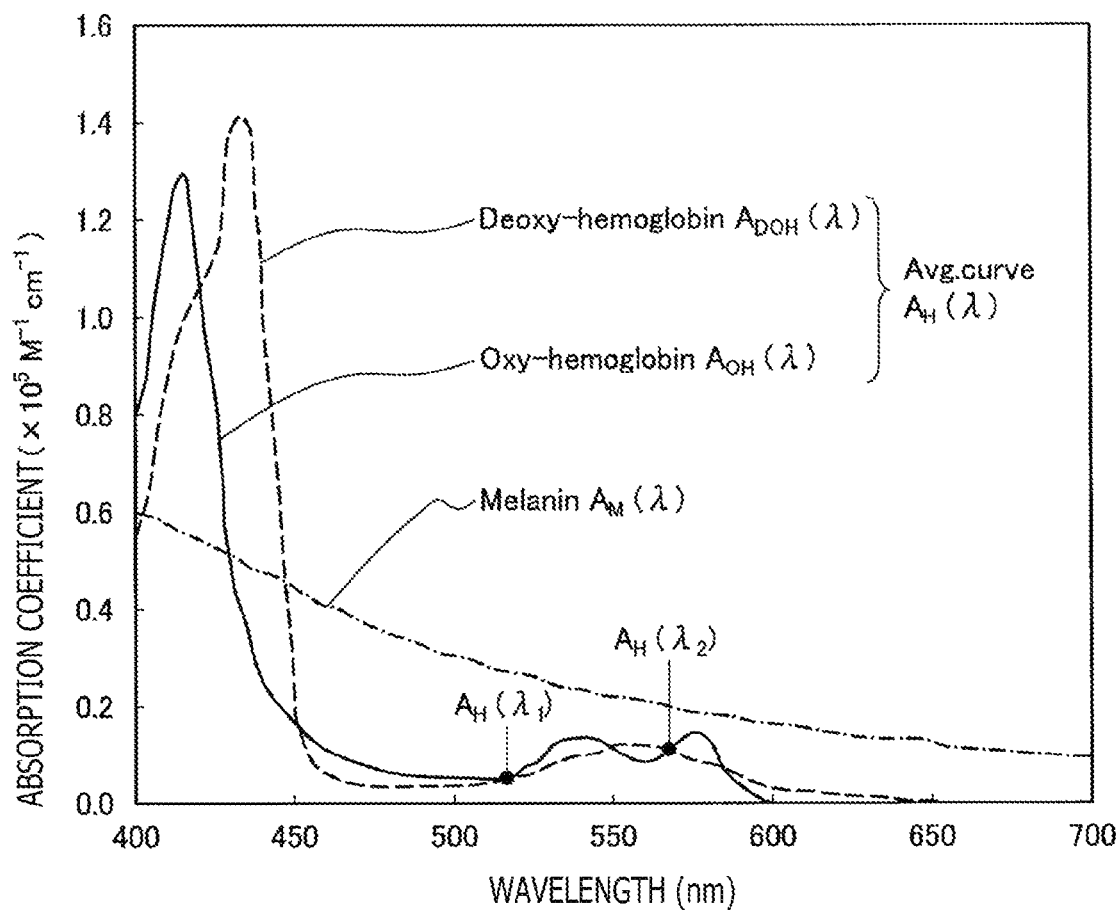
FIG. 5 is a diagram illustrating an example of absorbance coefficient spectral properties of skin pigments.

Accordingly, a description will be given below of an example of a method of suppressing (ideally, eliminating) the impact of a skin pigment by using a known absorbance coefficient spectral property of the pigment and performing a computational process that takes, as input, a plurality of pieces of spectral band data acquired as a multi-spectral image with particular emphasis on the case of eliminating the impact of hemoglobin. For example, FIG. 5 is a diagram illustrating an example of absorbance coefficient spectral properties of skin pigments. In FIG. 5, a horizontal axis represents the wavelength (nm). Also, a vertical axis represents the absorbance coefficient ($\times 10^5 M^{-1}$ $cm^{-1}$). Also, FIG. 5 depicts absorbance coefficient spectral properties of melanin (Melanin), oxidized hemoglobin (Oxy-hemoglobin), and deoxidized hemoglobin (Deoxy-hemoglobin), respectively.

In FIG. 5, we assume that a ratio between an absorbance coefficient A_H($\lambda$1) of hemoglobin at a wavelength $\lambda$1 and an absorbance coefficient A_H($\lambda$2) of hemoglobin at a wavelength $\lambda$2 is 1:1/X. At this time, the subtraction of a product of a measured absorbance $-\log 10(P(x,\lambda 2))$ at the wavelength $\lambda$2 by X from a measured absorbance $-\log 10(P(x,\lambda 1))$ at the wavelength $\lambda$1 is represented by the following calculation expression. That is, the calculation expression given below corresponds to a weighting computation (weighting process) for weighting the absorbance coefficient of hemoglobin between the wavelengths $\lambda$1 and $\lambda$2 on the basis of the weighting coefficient X appropriate to the above ratio. Also, one of the wavelengths $\lambda$1 and $\lambda$2 corresponds to an example of the "first wavelength" whereas the other wavelength corresponds to an example of the "second wavelength."

$$-(\log 10(P(x,\lambda 1))-X*\log 10(P(x,\lambda 2)))=$$
$$\{C\_M(x)*A\_M(\lambda 1)+C\_H(x)*A\_H(\lambda 1)+O(x,\lambda 1)\}-X*\{C\_M(x)*A\_M(\lambda 2)+*C\_H(x)*A\_H(\lambda 2)+O(x,\lambda 2)\}=C\_M(x)*(A\_M(\lambda 1)-X*A\_M(\lambda 2))+C\_H(x)*(A\_H(\lambda 1)-X*A\_H(\lambda 2))+(O(x,\lambda 1)-X*O(x,\lambda 2))=C\_M(x)*(A\_M(\lambda 1)-X*A\_M(\lambda 2))+(O(x,\lambda 1)-X*O(x,\lambda 2))$$
[Math. 4]

Accordingly, a feature value F1 is represented, for example, by the relational expression depicted as (Expression 4).

[Math. 5]

$$F1(x)=C\_M(x)*(A\_M(\lambda 1)-X*A\_M(\lambda 2))+(O(x,\lambda 1)-X*O(x,\lambda 2)) \quad \text{(Expression 4)}$$

Figure 6:
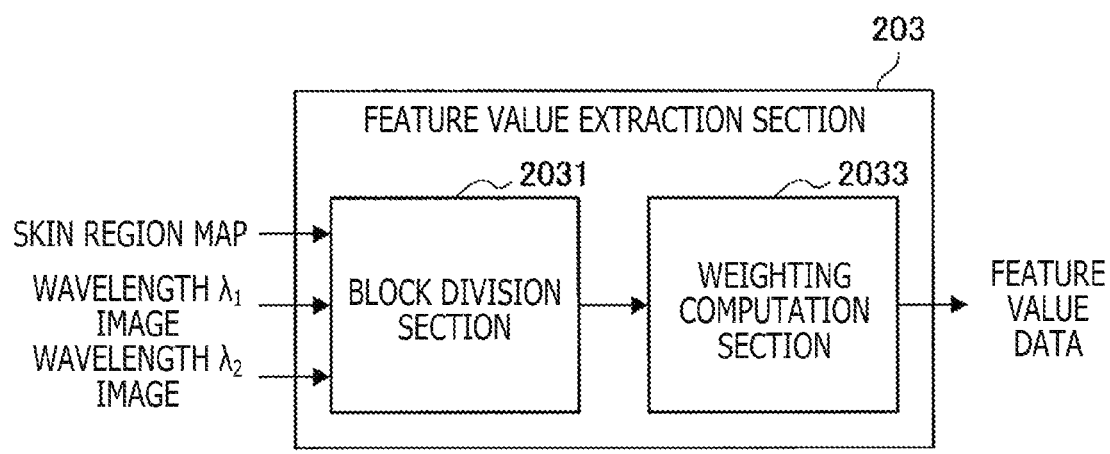
FIG. 6 is a block diagram illustrating an example of a functional configuration associated with calculation of a feature value according to the first embodiment.

Also, FIG. 6 is a block diagram illustrating an example of a functional configuration associated with calculation of a feature value according to the first embodiment of the present disclosure and is a diagram illustrating a more detailed configuration example of the feature value extraction section 203 of the information processing apparatus 200 depicted in FIG. 2 in a case where the above feature value F1 is extracted. As illustrated in FIG. 6, the feature value extraction section 203 includes a block division section 2031 and a weighting computation section 2033.

The block division section 2031 acquires data consistent with a detection result of a skin region from a multi-spectral image (hereinafter also referred to as a "skin region map"). Also, the block division section 2031 acquires, of a plurality of pieces of spectral band data acquired as a multi-spectral image, spectral band data (image) corresponding to the wavelength $\lambda$1 and spectral band data (image) corresponding to the wavelength $\lambda$2. The block division section 2031 divides, of each of the pieces of spectral band data corresponding to the wavelengths $\lambda$1 and $\lambda$2, the portion corresponding to the skin region on the basis of the skin region map into blocks of a given size.

Then, the block division section 2031 outputs, to the weighting computation section 2033, data of each block divided from each of the pieces of spectral band data corresponding to the wavelengths λ1 and λ2. As a specific example, in a case where one block is sized at eight by eight (8×8) (in pixels), as many pieces of the eight-by-eight pixel data as the number of divisions of the skin region are output to the weighting computation section 2033 for each of the wavelengths λ1 and λ2. It should be noted that the above size of one block is merely an example and is not necessarily limited to the above example.

The weighting computation section 2033 acquires, from the block division section 2031, data of each block divided from each of the pieces of spectral band data corresponding to the wavelengths λ1 and λ2. The weighting computation section 2033 performs a weighting computation (weighting process) based on the above (Expression 4) for each corresponding pixel by using, for each block, data corresponding to the wavelength λ1 and data corresponding to the wavelength λ2 as input. As a result, feature value data is generated that has calculation results of the feature value F1 mapped for each of the eight-by-eight pixels. As described above, the weighting computation section 2033 generates feature value data for each of the blocks into which the skin region has been divided and outputs the feature value data to a subsequent stage (e.g., recognition process section 205 illustrated in FIG. 2). That is, in the case of the above example, as many pieces of the eight-by-eight pixel data as the number of divisions of the skin region are output.

As described above, by using a known absorbance coefficient spectral property of hemoglobin and performing a computational process that takes a plurality of pieces of spectral band data acquired as a multi-spectral image as input, it is possible to eliminate the impact of hemoglobin that could otherwise cause noise. That is, the impact of the skin pigment that could otherwise cause noise for an identifier is cancelled, thus holding promise for improved accuracy and reliability associated with identification or authentication.

Figure 7:
FIG. 7 is a diagram illustrating an example of an extraction result of a first candidate feature value.

For example, FIG. 7 is a diagram illustrating an example of an extraction result of a first candidate feature value and depicts an example of an extraction result of a feature value based on the above (Expression 4) in a case where the user's hand is a subject. Specifically, the example illustrated in FIG. 5 assumes a case where the weighting coefficient X≈2 when Δ1=510 nm and λ2=570 nm. FIG. 6 illustrates an example of two-dimensionally arranged data (hereinafter referred to as a "feature value map") of calculation results of the feature value F1 at each portion of the skin region excluding the impact of hemoglobin under these conditions in accordance with the corresponding spatial position. In the feature value map illustrated in FIG. 7, the impact of melanin is primarily predominant with features such as "spots" and "slight redness" in the skin manifesting themselves qualitatively.

Similarly, it is possible to eliminate the impact of melanin by using a known absorbance coefficient spectral property of melanin and performing a computational process that takes, as input, a plurality of pieces of spectral band data acquired as a multi-spectral image. Specifically, a melanin distribution changes according to the extent of sunburn of the skin, and in the case of extraction of inherent information that can be used for personal recognition or identification from a captured skin image, melanin may translate into noise. Even in such a case, for example, the above computational process excludes the impact of melanin, thus canceling the impact of a variation in the skin color resulting from sunburn which can be noise for an identifier and holding promise for improved accuracy and reliability associated with identification or authentication.

An example of information distinctive to a subject (i.e., captured skin) extracted as a result of suppression of the impact of some skin pigments that has manifested itself within a multi-spectral image has been described above as a first candidate feature value together with the extraction method thereof.

(Second Candidate Feature Value)

A description will be given next of a second candidate feature value together with the extraction method thereof. In the first candidate feature value described above, the impact of a skin pigment is suppressed on the basis of the weighting computation (weighting process) that takes, as input, spectral band data in some wavelength bands and spectral band data in another wavelength band of a multi-spectral image of skin (two-dimensional spectral data). In contrast, the second candidate feature value is extracted by suppressing (canceling) the impact of two or more pigments. Specifically, the second candidate feature value is extracted by using, of a multi-spectral image (two-dimensional spectral data), spectral band data in N+1 or more wavelength bands and, thereby, suppressing the impact of N types of pigments. As a more specific example, it is possible to suppress the impact of two types of pigments by using spectral band data in three or more wavelength bands.

For example, in a case where hemoglobin is considered separately as oxidized hemoglobin and deoxidized hemoglobin, it is possible to extract, as feature values, the impact of only some pigments among melanin, oxidized hemoglobin, and deoxidized hemoglobin by using spectral band data in three or more wavelength bands. As a specific example, a second candidate feature value focusing on melanin can be extracted by using spectral band data in three or more wavelength bands, leaving out the melanin term, and deleting the oxidized hemoglobin and deoxidized hemoglobin terms. Also, it is possible, on the basis of a similar concept, to extract a second candidate feature value focusing on oxidized hemoglobin and a second candidate feature value focusing on deoxidized hemoglobin.

Specifically, from the Beer-Lambert law, the absorbance at the wavelength λ and at the spatial position x is represented by the relational expression given below as (Expression 5).

[Math. 6]

$$A(x,\lambda)=C\_(x)*A\_M(\lambda)+C\_Ho(x)*A\_Ho(\lambda)+C\_Hr(*A\_Hr(\lambda)+O(x,\lambda)$$ (Expression 5)

In the above (Expression 5), C_M(x), C_Ho(x), and C_Hr(x) represent the concentrations of melanin, oxidized hemoglobin, and deoxidized hemoglobin at the spatial position x, respectively. Also, A_M(λ), A_Ho(λ), and A_Hr(λ) represent the absorbance coefficients of melanin, oxidized hemoglobin, and deoxidized hemoglobin at the wavelength λ, respectively. It should be noted that respective properties of the absorbance coefficients of melanin, oxidized hemoglobin, and deoxidized hemoglobin are disclosed, for example, in the above Literature 3. Also, O(x,λ) represents the offset term that factors in the impact attributable to absorption and scattering by pigments other than melanin, oxidized hemoglobin, and deoxidized hemoglobin.

Also, by combining the above (Expression 5) and the (Expression 2) described earlier, the relationship between the measured spectral value and the pigment concentrations of melanin, oxidized hemoglobin, and deoxidized hemoglobin is represented by the relational expression given below as (Expression 6).

[Math. 7]

$$-\log 10(P(x,\lambda)) = C\_M(x)*A\_M(\lambda) + C\_Ho(x)*A\_Ho(\lambda) + C\_Hr(x)*A\_Hr(\lambda) + O(x,\lambda) \quad \text{(Expression 6)}$$

From the above (Expression 6), it is understood that individual differences (i.e., differences in skin color unevenness between individuals) occur due to differences in spatial distribution of melanin, oxidized hemoglobin, and deoxidized hemoglobin concentrations (C_M(x), C_Ho(x), and C_Hr (x)).

Also, a calculation expression is derived, on the basis of three or more pieces of band data of the plurality of pieces of spectral band data acquired as a multi-spectral image and the above (Expression 6), that suppresses (ideally, eliminates) the impact of some pigments among melanin, oxidized hemoglobin, and deoxidized hemoglobin. For example, the following calculation expression is derived by using spectral band data at wavelengths λ1, λ2, and λ3.

$$-\log 10(P(x,\lambda1)) = C\_M(x)*A\_M(\lambda1) + C\_Ho(x)*A\_Ho(\lambda1) + C\_Hr(x)*A\_Hr(\lambda1) + O(x,\lambda1)$$

$$-\log 10(P(x,\lambda2)) = C\_M(x)*A\_M(\lambda2) + C\_Ho(x)*A\_Ho(\lambda2) + C\_Hr(x)*A\_Hr(\lambda2) + O(x,\lambda2)$$

$$-\log 10(P(x,\lambda3)) = C\_M(x)*A\_M(\lambda3) + C\_Ho(x)*A\_Ho(\lambda3) + C\_Hr(x)*A\_Hr(\lambda3) + O(x,\lambda3) \quad \text{[Math. 8]}$$

By using the above calculation expression and known absorption spectral properties of some pigments among melanin, oxidized hemoglobin, and deoxidized hemoglobin (refer, for example, to FIG. 5), it is possible to extract a feature value map with suppressed (ideally, eliminated) impact of some of the pigments in question.

As a specific example, the ratio between A_Ho(λ1), A_Ho(λ2), and A_Ho(λ3) and the ratio between A_Hr(λ1), A_Hr(λ2), and A_Hr(λ3) are derived on the basis of the known absorption spectral properties of oxidized hemoglobin and deoxidized hemoglobin illustrated in FIG. 5. Then, a weighting computation (weighting process) is performed to weight the absorbance coefficients of oxidized hemoglobin and deoxidized hemoglobin between the wavelengths λ1, λ2, and λ3 on the basis of the weighting coefficients appropriate to the derivation results of the above ratios, thus making it possible to extract a melanin feature value map with suppressed (ideally, eliminated) impact of oxidized hemoglobin and deoxidized hemoglobin.

Also, it is possible, on the basis of a similar concept, to extract an oxidized hemoglobin feature value map with suppressed impact of melanin and deoxidized hemoglobin or a deoxidized hemoglobin feature value map with suppressed impact of melanin and oxidized hemoglobin. Also, in a case where attention is focused on melanin, oxidized hemoglobin, and deoxidized hemoglobin, a spectral band with peaks at 470 nm, 530 nm, and 560 nm as λ1, λ2, and λ3, respectively (or in their vicinities), for example, is preferably used.

An example of information distinctive to a subject (i.e., captured skin) extracted as a result of suppression (cancel) of the impact of two or more pigments has been described above as a second candidate feature value together with the extraction method thereof.

(Third Candidate Feature Value)

A description will be given next, as a third candidate feature value, of another example of information distinctive to a subject (i.e., captured skin) with emphasis on some pigments among a plurality of pigments as done with the second candidate feature value described above, with particular emphasis on the extraction method thereof.

A description was made regarding the second candidate feature value to the effect that it is possible to extract a feature value map with the impact of deoxidized hemoglobin left unremoved among melanin, oxidized hemoglobin, and deoxidized hemoglobin (i.e., feature value map with the impact of melanin and oxidized hemoglobin suppressed). The third candidate feature value can be extracted, as a feature value similar to the second candidate feature value, by a simpler method than the method for the second candidate feature value.

Specifically, as disclosed in Literature 4 described above, deoxidized hemoglobin is characterized by high absorbance and low scattering and reflection (spectral properties) in the near-infrared band (in particular, the wavelength band in the vicinity of 760 nm wavelength). By using such properties, it is possible to extract a feature value of deoxidized hemoglobin as a third candidate feature value, for example, by using, of a plurality of pieces of spectral band data acquired as a multi-spectral image, spectral band data in the vicinity of 760 nm. For example, a third candidate feature value F3 focusing on deoxidized hemoglobin can be extracted on the basis of the relational expression given below as (Expression 7).

[Math. 9]

$$F3(x) = -\log 10(P(x,\lambda)) \text{ where } \lambda = 760 \quad \text{(Expression 7)}$$

Figure 8:
FIG. 8 is a diagram illustrating an example of an extraction result of a third candidate feature value.

For example, FIG. 8 is a diagram illustrating an example of an extraction result of a third candidate feature value and depicts an example of an extraction result of a feature value based on the above (Expression 7) in the case where the user's hand is a subject.

It should be noted that although the case was described above where attention was focused on deoxidized hemoglobin, there is a case where a third candidate feature value can be extracted for other pigments by using a technique based on a similar concept. Specifically, by using wavelength band data with a target pigment demonstrating a distinctive spectral property, i.e., spectral band data in the wavelength band offering high absorbance and low scattering and reflection, it is possible to extract a third candidate feature value focusing on the pigment in question.

Another example of information distinctive to a subject (i.e., captured skin) has been described above as a third candidate feature value with emphasis on some pigments among a plurality of pigments as done with the second candidate feature value described above, with particular emphasis on the extraction method thereof.

(Fourth Candidate Feature Value)

A description will be given next of a fourth candidate feature value. The first candidate feature value to the third candidate feature value described earlier are feature values extracted with focus on a certain spatial position. In contrast, the fourth candidate feature value is a feature value extracted with focus on a variation in absorbance in a spatial direction and is characterized by higher robustness to the change in a light source. Accordingly, the fourth candidate feature value will be described below with particular emphasis on the extraction method thereof.

Spectral data R observed from the imaging section such as a camera (in other words, image sensor) is generally determined by a spectral distribution E of light irradiated from a light source, a spectral reflectance S of a subject, and a spectral sensitivity property Q of the camera (multi-spectral camera). Specifically, the above spectral data R is represented by the relational expression given below as (Expression 8).

[Math. 10]

$$R_k = \alpha \int E(\lambda) S(\lambda) Q_k(\lambda) d\lambda \quad \text{(Expression 8)}$$

In the above (Expression 8), α represents a scaling factor. Also, λ represents the wavelength of light, and k represents the number of color channels associated with image capture by the imaging section.

As is understood with reference to the above (Expression 8), in the event of fluctuation of the spectral distribution E of light irradiated from the light source, the value observed by the imaging section may change even if the subject has the same spectral reflectance S. That is, different pieces of data may be acquired as the spectral data R consistent with the observation result in question. The fourth candidate feature value makes it possible to ensure the identity of the extraction result in a more suitable manner even in the presence of fluctuation of the spectral distribution E of light irradiated from the light source as described here.

The extraction method of the fourth candidate feature value will be described below in more detail. In a case where attention is focused on the wavelength λ, the spatial variation between the absorbance at a spatial position x1 and the absorbance at a spatial position x2 different from the spatial position x1 is represented by the relational expression given below on the basis of the above (Expression 3).

$$-\{\log 10(P(x1,\lambda)) - \log 10(P(x2,\lambda))\} = \{C\_M(x1)*A\_M(\lambda) + C\_H(x1)*A\_H(\lambda) + O(x1,\lambda)\} - \{C\_M(x2)*A\_M(\lambda) + C\_H(x2)*A\_H(\lambda) + O(x2,\lambda)\} = A\_M(\lambda)*(C\_M(x1) - C\_M(x2)) + A\_H(\lambda)*(C\_H(x1) - C\_H(x2)) + (O(x1,\lambda) - O(x2,\lambda)) \quad \text{[Math. 11]}$$

At this time, if the feature value at each coordinate x is represented as a difference from a reference point xc, a fourth candidate feature value F4 is represented by the relational expression given below as (Expression 9).

[Math. 12]

$$F4(x,\lambda) = A\_M(\lambda)*(C\_M(x) - C\_M(xc)) + A\_H(\lambda)*(C\_H(x) - C\_H(xc)) + (O(x,\lambda) - O(xc,\lambda)) \quad \text{(Expression 9)}$$

Figure 9:
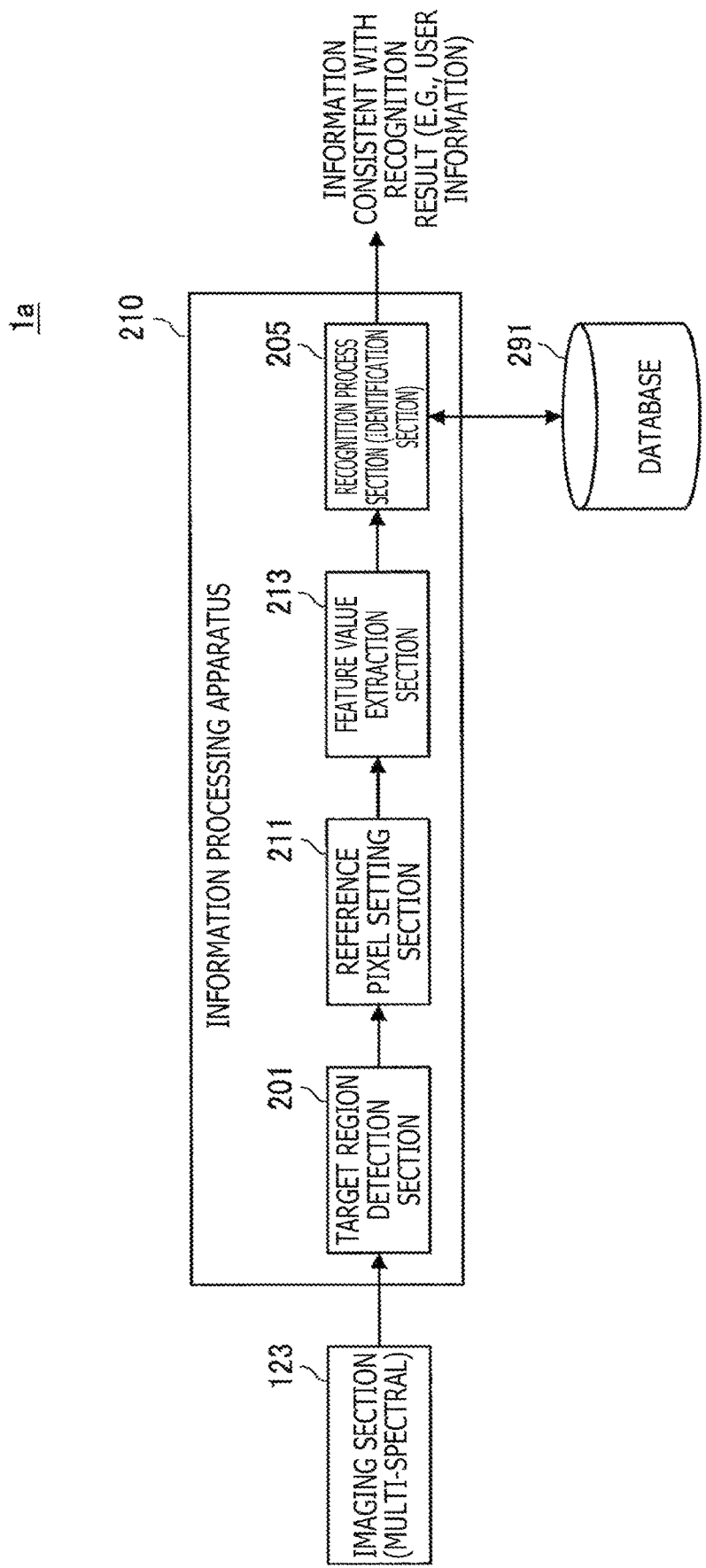
FIG. 9 is a block diagram illustrating another example of the functional configuration of the information processing apparatus according to the first embodiment.

A description will be given here of an example of a functional configuration of the information processing apparatus according to the present embodiment with reference to FIG. 9. FIG. 9 is a block diagram illustrating another example of a functional configuration of the information processing apparatus according to the present embodiment. It should be noted that, in the description given hereinafter, the information processing system illustrated in FIG. 9 may be referred to as an "information processing system 1a" for distinction from the information processing system 1 described with reference to FIG. 2. Also, in a case where no distinction is made therebetween, the information processing system may be simply referred to as the "information processing system 1."

As illustrated in FIG. 9, the information processing system 1a includes the imaging section 123, an information processing apparatus 210, and the database 291. Also, the information processing apparatus 210 includes the target region detection section 201, a reference pixel setting section 211, a feature value extraction section 213, and the recognition process section 205. It should be noted that the imaging section 123, the database 291, the target region detection section 201, and the recognition process section 205 are substantially similar to the imaging section 123, the database 291, the target region detection section 201, and the recognition process section 205 illustrated in FIG. 2, respectively, and accordingly, a detailed description thereof will be omitted.

The reference pixel setting section 211 sets, of a target region (e.g., skin region) detected from a multi-spectral image consistent with an imaging result of the imaging section 123, some pixels as a reference point xc. Then, the reference pixel setting section 211 outputs, to the feature value extraction section 213, information regarding the target region in question with the reference point xc set therein.

The feature value extraction section 213 acquires, from the reference pixel setting section 211, information regarding the target region with the reference point xc set therein and performs, on the target region in question, an analytic process appropriate to the absorption spectral property of a given pigment, thus extracting a feature value. Specifically, the feature value extraction section 213 extracts, for each portion of the target region, a feature value as a difference from a reference point wc on the basis of the above (Expression 9). As described above, the feature value extraction section 213 extracts feature values from the multi-spectral image and outputs information regarding the feature values in question (e.g., feature value map) to the recognition process section 205. It should be noted that the subsequent processes are similar to those performed by the information processing system 1 described with reference to FIG. 2 and, accordingly, a detailed description thereof will be omitted.

An example of a functional configuration of the information processing apparatus according to the present embodiment has been described above with reference to FIG. 9.

Figure 10:
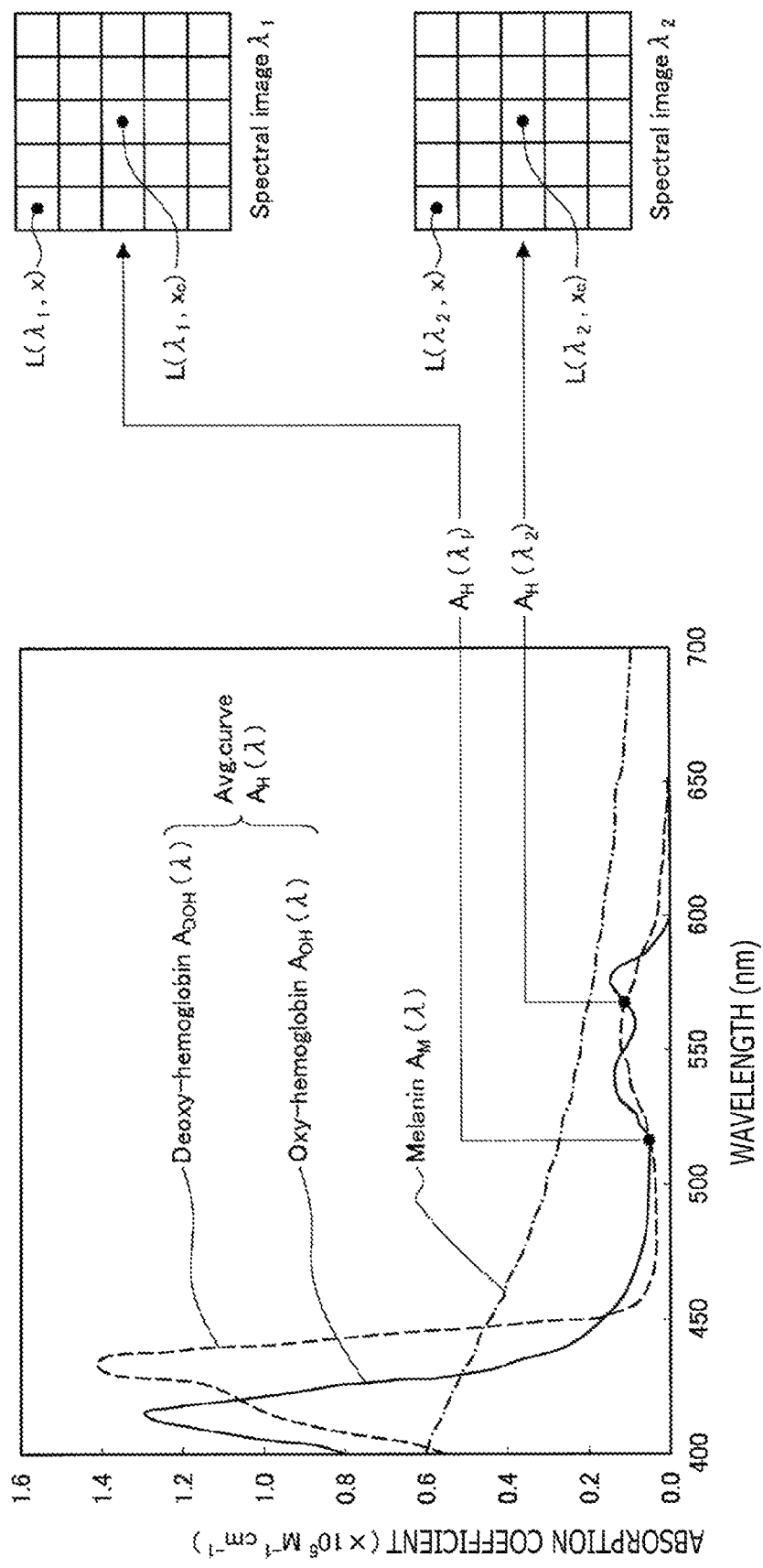
FIG. 10 is a diagram outlining an example of a case in which the first candidate feature value and a fourth candidate feature value are used.

It should be noted that the fourth candidate feature value can also be used in combination with each of the above first candidate feature value to the third candidate feature value. As a specific example, following the extraction of a variation in the absorbance in the spatial direction (fourth candidate feature value), a feature value with suppressed impact of a given pigment (e.g., first candidate feature value) may be extracted on the basis of a computational process that takes, as input, a plurality of different pieces of spectral band data. For example, FIG. 10 is a diagram outlining an example of a case in which the first candidate feature value and the fourth candidate feature value are used. Also, the following relational expression is derived from the above (Expression 4) and (Expression 9).

$$-[\{\log 10(P(x,\lambda 1)) - \log 10(P(xc,\lambda 1))\} - X*\{\log 10(P(x,\lambda 2)) - \log 10(P(xc,\lambda 2))\}] = \{A\_M(\lambda 1)*(C\_M(x) - C\_M(xc)) + A\_H(\lambda 1)*(C\_H(x) - C\_H(xc)) + (O(x,\lambda 1) - O(xc,\lambda 1))\} - X*\{A\_M(\lambda 2)*(C\_M(x) - C\_M(xc)) + A\_H(\lambda 2)*(C\_H(x) - C\_H(xc)) + (O(x,\lambda 2) - O(xc,\lambda 2))\} = (A\_M(\lambda 1) - X*A\_M(\lambda 2))*(C\_M(x) - C\_M(xc)) + (A\_H(\lambda 1) - X*A\_H(\lambda 2))*(C\_H(x) - C\_H(xc)) + (O(x,\lambda 1) - O(xc,\lambda 1)) - X*(O(x,\lambda 2) - O(xc,\lambda 2)) \quad \text{[Math. 13]}$$

The relational expression given below as (Expression 10) is derived by selecting, in the above relational expression, the weighting coefficient X that satisfies the condition $A\_H(\lambda 1) = X*A\_H(\lambda 2)$.

[Math. 14]

$$F14(x) = (\lambda\_M(\lambda 1) - X*A\_M(\lambda 2))*(C\_M(x) - C\_M(xc)) + (O(x,\lambda 1) - O(xc,\lambda 1)) - X*(O(x,\lambda 2) - O(xc,\lambda 2)) \quad \text{(Expression 10)}$$

The extraction of a feature value as described above allows, for example, for suppression (ideally, elimination) of the impact of hemoglobin and further extraction of a feature value independent of fluctuation of the spectral distribution of light irradiated from the light source at the time of capture of a multi-spectral image. That is, by performing personal identification by using feature values as described above, it is possible to realize personal recognition that offers high robustness to the change in feature value over time caused by the impact of hemoglobin and the change in spectral distribution of light irradiated from a light source over time.

An example of a feature value extracted as a fourth candidate feature value with focus on a variation in absorbance in the spatial direction has been described above with particular emphasis on the extraction method thereof.

<3.3. Second Embodiment>

A description will be given next of a second embodiment of the present disclosure. An information processing system according to the second embodiment calculates, on the basis of correlation between an image acquired in the past (multi-spectral image) and a current image, a motion vector in the region of the image in question, thus extracting a variation in the absorption spectral property in a time direction and using the variation as a feature value. It should be noted that, in the description given hereinafter, the feature value in question will be also referred to as a "fifth candidate feature value" for reasons of convenience for distinction from other feature values described earlier.

<3.3.1. Functional Configuration>

Figure 11:
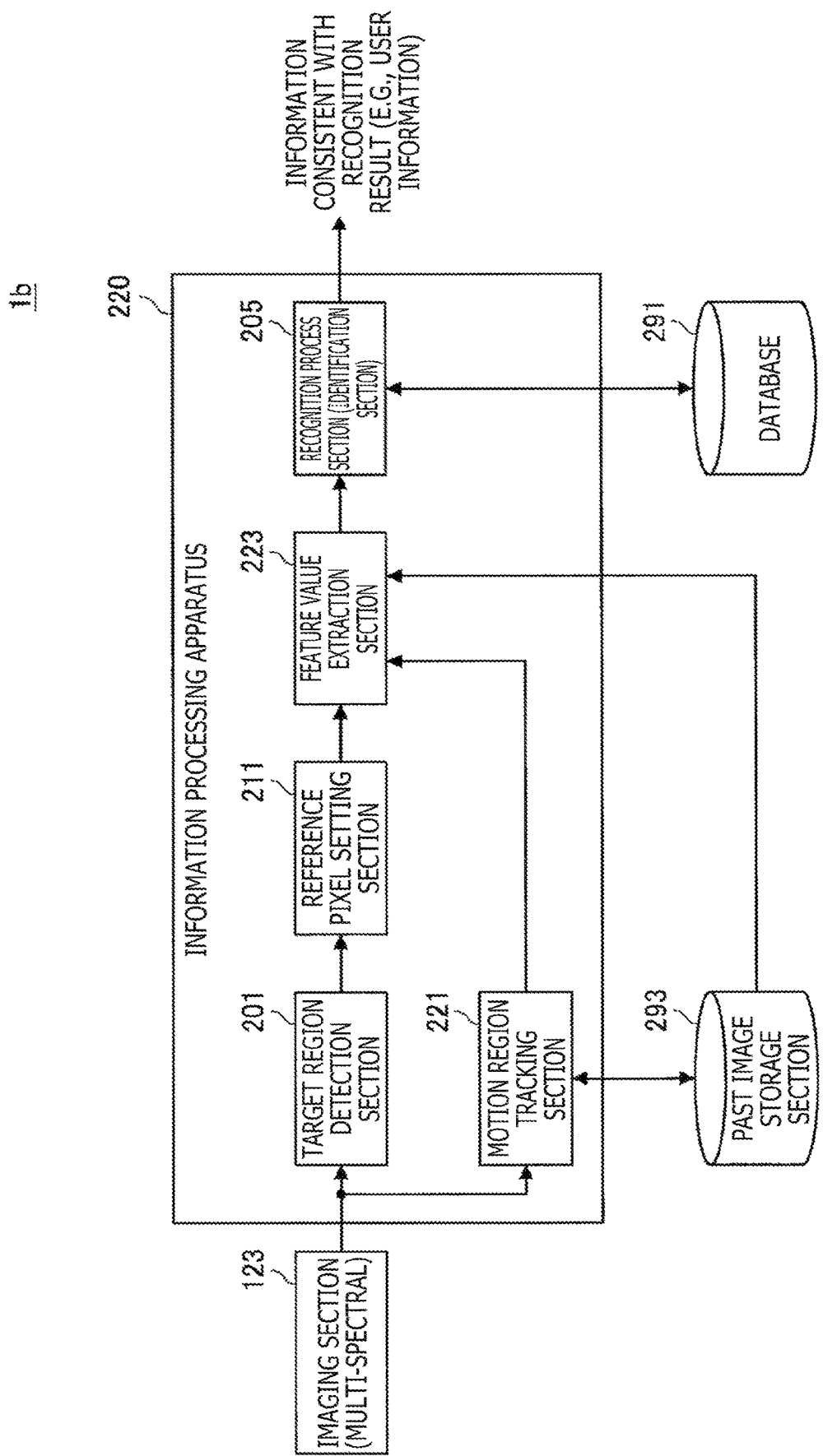
FIG. 11 is a block diagram illustrating an example of a functional configuration of an information processing system according to a second embodiment of the present disclosure.

A description will be given first, with reference to FIG. 11, of an example of a functional configuration of an information processing system according to the second embodiment of the present disclosure. FIG. 11 is a block diagram illustrating an example of a functional configuration of the information processing system according to the present embodiment. It should be noted that, in the description given hereinafter, the information processing system illustrated in FIG. 11 may be referred to as an "information processing system 1b" for distinction from the information processing systems according to the other embodiments described earlier. Also, in a case where no distinction is made therebetween, the information processing system may be simply referred to as the "information processing system 1."

As illustrated in FIG. 11, the information processing system 1b includes the imaging section 123, an information processing apparatus 220, the database 291, and a past image storage section 293. Also, the information processing apparatus 220 includes the target region detection section 201, the reference pixel setting section 211, a motion region tracking section 221, a feature value extraction section 223, and the recognition process section 205. It should be noted that the imaging section 123, the database 291, the target region detection section 201, the reference pixel setting section 211, and the recognition process section 205 are substantially similar to the imaging section 123, the database 291, the target region detection section 201, the reference pixel setting section 211, and the recognition process section 205 illustrated in FIG. 9, respectively, and accordingly, a detailed description thereof will be omitted.

The motion region tracking section 221 calculates, for each region of the image, correlation between an image acquired in the past (multi-spectral image) and a current image (multi-spectral image) consistent with an imaging result of the imaging section 123. The motion region tracking section 221 searches the current image for the region most correlated with a region of the image acquired in the past, thus generating data having motion vectors of the region in question two-dimensionally mapped therein (hereinafter also referred to as a "motion vector map"). Then, the motion region tracking section 221 outputs the generated motion vector map to the feature value extraction section 223.

The feature value extraction section 223 calculates a motion vector for each block into which the skin region map consistent with a detection result of the skin region has been divided, thus extracting a feature value (fifth candidate feature value) on the basis of the calculation result of the motion vector in question. For example, the feature value extraction section 223 may calculate a general optical flow as the above motion vector. It should be noted that the motion vector in question is particularly preferably robust to a spectral change between blocks, and for example, NCC (Normalized Cross Correlation) or ZNCC (Zero means Normalized Cross Correlation) is preferably applied to a process after spatial edge extraction and an evaluation index. It should be noted that the calculation of a spectral change between corresponding blocks (in other words, spectral change between different times of day for a certain block) is synonymous with the calculation of a variation in absorption spectral property in the time direction. Specifically, the feature value extraction section 223 desirably identifies, on the basis of the motion vector map generated by the motion region tracking section 221, corresponding blocks (e.g., blocks corresponding to certain part of the skin region) in images acquired at different times. That is, the feature value extraction section 223 identifies, on the basis of the motion vector map, corresponding blocks in images acquired at different times. Then, the feature value extraction section 223 need only compare the absorption spectral properties of the corresponding blocks in the images in question, thus extracting a variation in the absorption spectral property in the time direction as a feature value (fifth candidate feature value). It should be noted that details of the feature value calculation method will be described separately later. The feature value extraction section 213 extracts a feature value from the multi-spectral image as described above and outputs information regarding the feature value in question (e.g., feature value map) to the recognition process section 205. It should be noted that the subsequent processes are similar to those performed by the information processing system 1 described with reference to FIG. 2 and, accordingly, a detailed description thereof will be omitted.

An example of a functional configuration of the information processing system according to the second embodiment of the present disclosure has been described above with reference to FIG. 11.

<3.3.2. Details of Feature Value>

Next, a detailed description will be given bellow of the fifth candidate feature value together with the extraction method thereof.

For example, incorporation of a time variable t into the above (Expression 3) is represented by the relational expression given below as (Expression 11).

[Math. 15]

$$-\log 10(P(x,t,\lambda)) = C\_M(x,t) * A\_M(\lambda) + C\_OH(x,t) \\ * A\_OH(\lambda) + C\_DOH(x,t) * A\_DOH(\lambda) + O(x,t,\lambda) \quad \text{(Expression 11)}$$

It should be noted that oxidized hemoglobin and deoxidized hemoglobin are considered separately in the above (Expression 11). Specifically, in the above (Expression 11), C_OH and A_OH represent the concentration and the absorbance coefficient of oxidized hemoglobin, respectively. Also, C_DOH and A_DOH represent the concentration and the absorbance coefficient of deoxidized hemoglobin, respectively.

The variation in absorbance between time t1 and time t2 at the wavelength λ and the spatial position x is represented by the following relational expression.

$$-\{\log 10(P(x,t1,\lambda))-\log 10(P(x,t2,\lambda))\}=\{C\_M(x,t1)\\*A\_M(\lambda)+C\_OH(x,t1)*A\_OH(\lambda)+C\_DOH(x,t1)\\*A\_DOH(\lambda)+O(x,t1,\lambda)\}-\{C\_M(x,t2)*A\_M(\lambda)+\\C\_OH(x,t2)*A\_OH(\lambda)+C\_DOH(x,t2)*A\_DOH\\(\lambda)+O(x,t2,\lambda)\}=A\_M(\lambda)*(C\_M(x,t1)-C\_M(x,\\t2))+A\_OH(\lambda)*(C\_OH(x,t1)-C\_OH(x,t2))+\\A\_DOH(\lambda)*(C\_DOH(x,t1)-C\_DOH(x,t2))+(O(x,\\t1,\lambda)O(x,t2,\lambda))$$ [Math. 16]

Assuming here that the concentrations of substances other than hemoglobin remain nearly unchanged in the spatial position x in a short period of time, it is possible to consider that the following relational expression holds.

$$(C\_M(x,t1)=C\_M(x,t2), O(x,t1,\lambda)=O(x,t2,\lambda))$$ [Math. 17]

Therefore, the following relational expression holds.

$$-\{\log 10(P(x,t1,\lambda))-\log 10(P(x,t2,\lambda))\}=A\_OH(\lambda)*\\(C\_OH(x,t1)-C\_OH(x,t2))+A\_DOH(\lambda)*\\(C\_DOH(x,t1)-C\_DOH(x,t2))$$ [Math. 18]

At this time, for example, it is possible to consider that, on the basis of the absorbance coefficient spectral properties of skin pigments illustrated in FIG. 5, the following relationship holds at the wavelength λ in the vicinity of 570 nm.

$$A\_OH(\lambda)=A\_DOH(\lambda)=A\_H(\lambda)=Y(\text{const})$$ [Math. 19]

Therefore, a fifth candidate feature value F5 is represented by the relational expression given below as (Expression 12).

[Math. 20]

$$F5(x,t1)=-\{\log 10(P(x,t1,\lambda))-\log 10(P(x,t2,\lambda))\}=Y*\{\\(C\_OH(x,t1)-C\_OH(x,t2))+(C\_DOH(x,t1)-\\C\_DOH(x,t2))\} \text{ Where } Y=A\_H(\lambda=570)$$ (Expression 12)

The feature value consistent with the difference of the change over time between oxidized hemoglobin concentration and deoxidized hemoglobin concentration (fifth candidate feature value) calculated as described above may be used for personal identification or authentication.

Also, the change in hemoglobin over time is easier to detect in a region with high absorbance of hemoglobin in question (i.e., region in the multi-spectral image). Accordingly, for example, by adding, as spectral band data acquired as a multi-spectral image, wavelength band data having a frequency in the vicinity of 425 nm as a center frequency, it is possible to acquire a feature value with a more highlighted distinctive portion. That is, it is possible to acquire a feature value with a more highlighted distinctive portion by calculating, in the above (Expression 12), the fifth candidate feature value F5 as the wavelength λ of 425 nm.

<3.3.3. Working Example>

Figure 12:
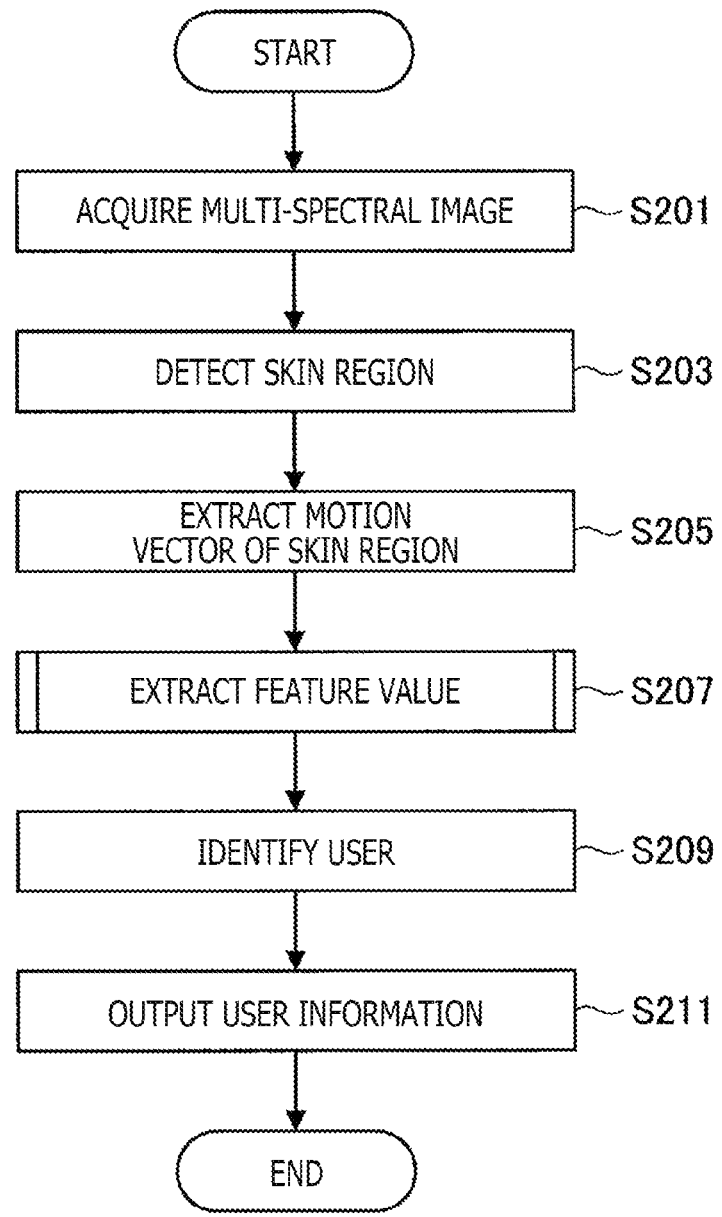
FIG. 12 is a flowchart illustrating an example of a flow of a series of processes handled by an information processing system according to the second embodiment.

A description will be given next of a working example of the information processing system according to the present embodiment. In the present working example, a description will be given of examples of processes performed in a case where user identification or authentication is carried out by combining, with a fourth candidate feature value, first, third, and fifth candidate feature values extracted from a multi-spectral image of the user's skin as a subject and using these feature values. For example, FIG. 12 is a flowchart illustrating an example of a flow of a series of processes handled by the information processing system according to the present embodiment.

In the present working example, the imaging section 123 can acquire, as a multi-spectral image, spectral band data corresponding to six wavelength bands whose respective center wavelengths are generally equal to 425 nm, 510 nm, 570 nm, 760 nm, 870 nm, and 970 nm. On the basis of such a configuration, the information processing apparatus 220 according to the present working example acquires a multi-spectral image consistent with the imaging result of the subject from the imaging section 123 (S201).

Next, the information processing apparatus 220 (target region detection section 201) performs image analysis on the acquired multi-spectral image, thus detecting a skin region from the multi-spectral image in question (S203).

As a specific example, the information processing apparatus 220 extracts a skin color region captured in the multi-spectral image through HSV conversion using spectral band data corresponding to the wavelengths of 425 nm, 510 nm, and 570 nm, respectively. The result of the extraction in question will be also referred to as a first extraction result for reasons of convenience. Also, the information processing apparatus 220 extracts a skin color region captured in the multi-spectral image in question on the basis of the difference between the pieces of spectral band data for 870 nm and 970 nm. The result of the extraction in question will be also referred to as a second extraction result for reasons of convenience. Then, the information processing apparatus 220 merges the above first extraction result and the above second extraction result, thus detecting the skin region from the multi-spectral image. As a specific example, the information processing apparatus 220 may detect, as a skin region, the region of the multi-spectral image identified by a set intersection between the above first extraction result and the above second extraction result.

Next, the information processing apparatus 220 (motion region tracking section 221) extracts motion vectors of the blocks into which the skin region has been divided (S205). Then, the information processing apparatus 220 (feature value extraction section 223) performs, on the skin region detected from the multi-spectral image, an analytic process appropriate to the absorption spectral property of a given skin pigment (e.g., melanin or hemoglobin), thus detecting a feature value (S207).

Figure 13:
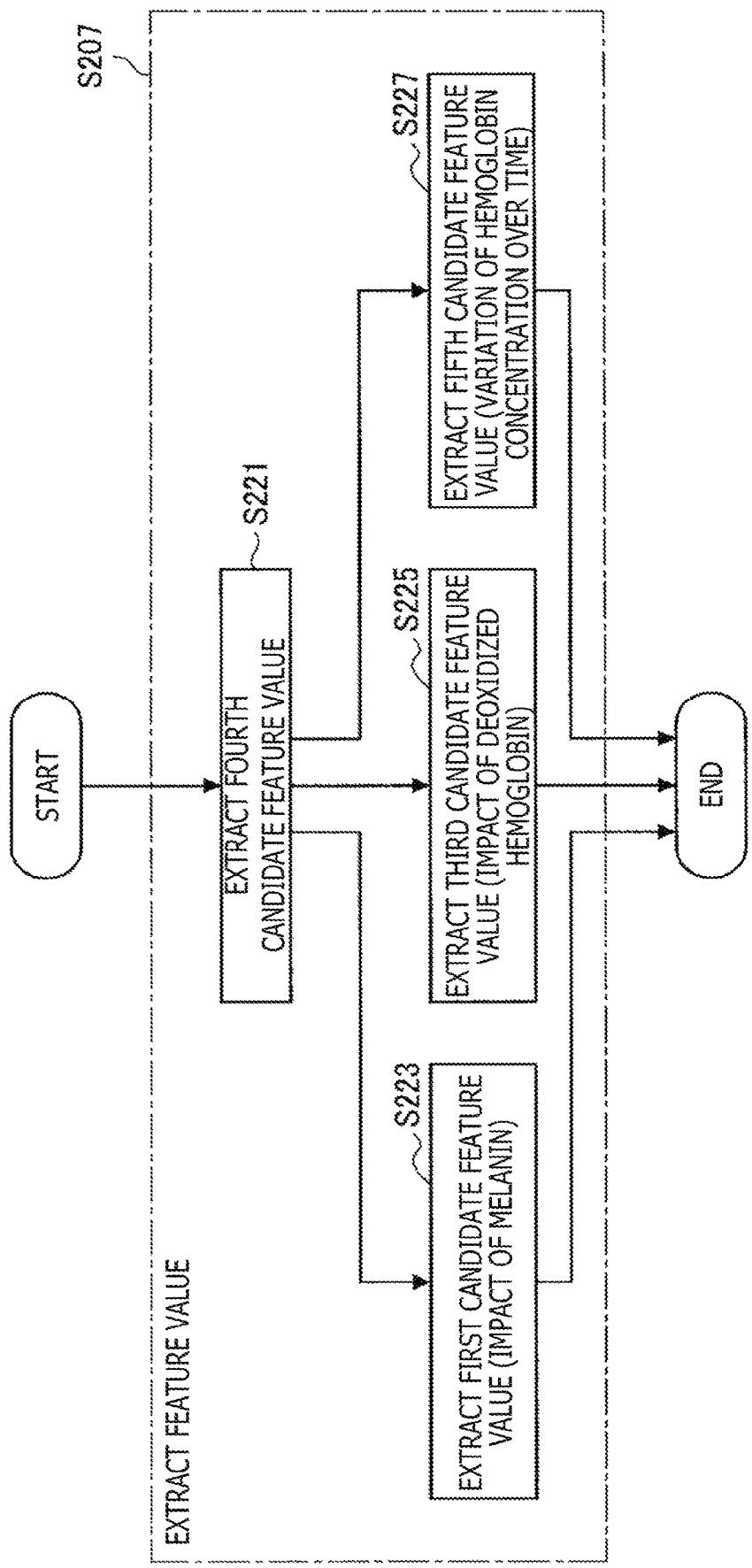
FIG. 13 is a flowchart illustrating examples of processes associated with extraction of feature values by the information processing system according to the second embodiment.

A description will be given here of examples of processes for extracting a feature value in accordance with the spectral property of a given skin pigment from the skin region detected from a multi-spectral image with reference to FIG. 13. FIG. 13 is a flowchart illustrating examples of processes associated with extraction of feature values by the information processing system according to the working example of the present embodiment.

As illustrated in FIG. 13, the information processing apparatus 220 sets some pixels of the skin region detected from a multi-spectral image as a reference point. Then, the information processing apparatus 220 extracts a fourth candidate feature value for each of the wavelengths of 425 nm, 510 nm, 570 nm, 760 nm, 870 nm, and 970 nm from the skin region in question, thus generating a feature value map F4 on the basis of the extraction results in question. Specifically, the information processing apparatus 220 extracts, for each portion of the skin region, a fourth candidate feature value as a difference from the reference point wc on the basis of the above (Expression 9), thus generating the feature value map F4 on the basis of the extraction results in question (S221).

Next, the information processing apparatus 220 updates the feature value maps F4 generated, respectively, for the wavelengths of 510 nm and 570 nm on the basis of the above (Expression 4) (S223). That is, the post-update feature value maps F4 correspond to first candidate feature values with predominant melanin impact. It should be noted that, in the description given hereinafter, the post-update feature value maps F4 in question will be also referred to as "feature value maps F14" for reasons of convenience.

Also, the information processing apparatus 220 updates the feature value map F4 generated for the wavelength of 760 nm on the basis of the above (Expression 7) (S225). That is, the post-update feature value map F4 corresponds to a third candidate feature value with focus on the impact of deoxidized hemoglobin. It should be noted that, in the description given hereinafter, the post-update feature value map F4 in question will be also referred to as a "feature value map F34" for reasons of convenience.

Also, the information processing apparatus 220 updates the feature value map F4 generated for the wavelength of 425 nm on the basis of the above (Expression 12) (S225). That is, the post-update feature value map F4 corresponds to a fifth candidate feature value with focus on the change in hemoglobin concentration over time. It should be noted that, in the description given hereinafter, the post-update feature value map F4 in question will be also referred to as a "feature value map F54" for reasons of convenience.

Next, as depicted in FIG. 12, the information processing apparatus 220 (recognition process section 205) checks each of the above feature values (i.e., feature value maps F14, F34, and F54) against data stored in advance in a given storage region (e.g., database 291), thus carrying out user identification or authentication (S209). As a specific example, user identification or authentication may be carried out by inputting each of the feature values extracted into a recognizer that has learnt the relationship between each of the feature values in question and the user on the basis of machine learning. Then, the information processing apparatus 220 (recognition process section 205) outputs, to a given output destination, information regarding the user in question (e.g., user ID) in accordance with the result of user identification or authentication (S211).

As a working example, examples of processes have been described above that are performed in a case where user identification or authentication is carried out by combining, with a fourth candidate feature value, first, third, and fifth candidate feature values extracted from a multi-spectral image of the user's skin as a subject and using these feature values.

<3.4. Third Embodiment>

A description will be given next of a third embodiment of the present disclosure. An information processing system according to the third embodiment selectively switches between wavelengths of light irradiated on an imaging region (real space region) whose multi-spectral image is to be captured, thus allowing for extraction of a feature value from the multi-spectral image in question in a more suitable manner.

<3.4.1. Schematic Configuration>

Figure 14:
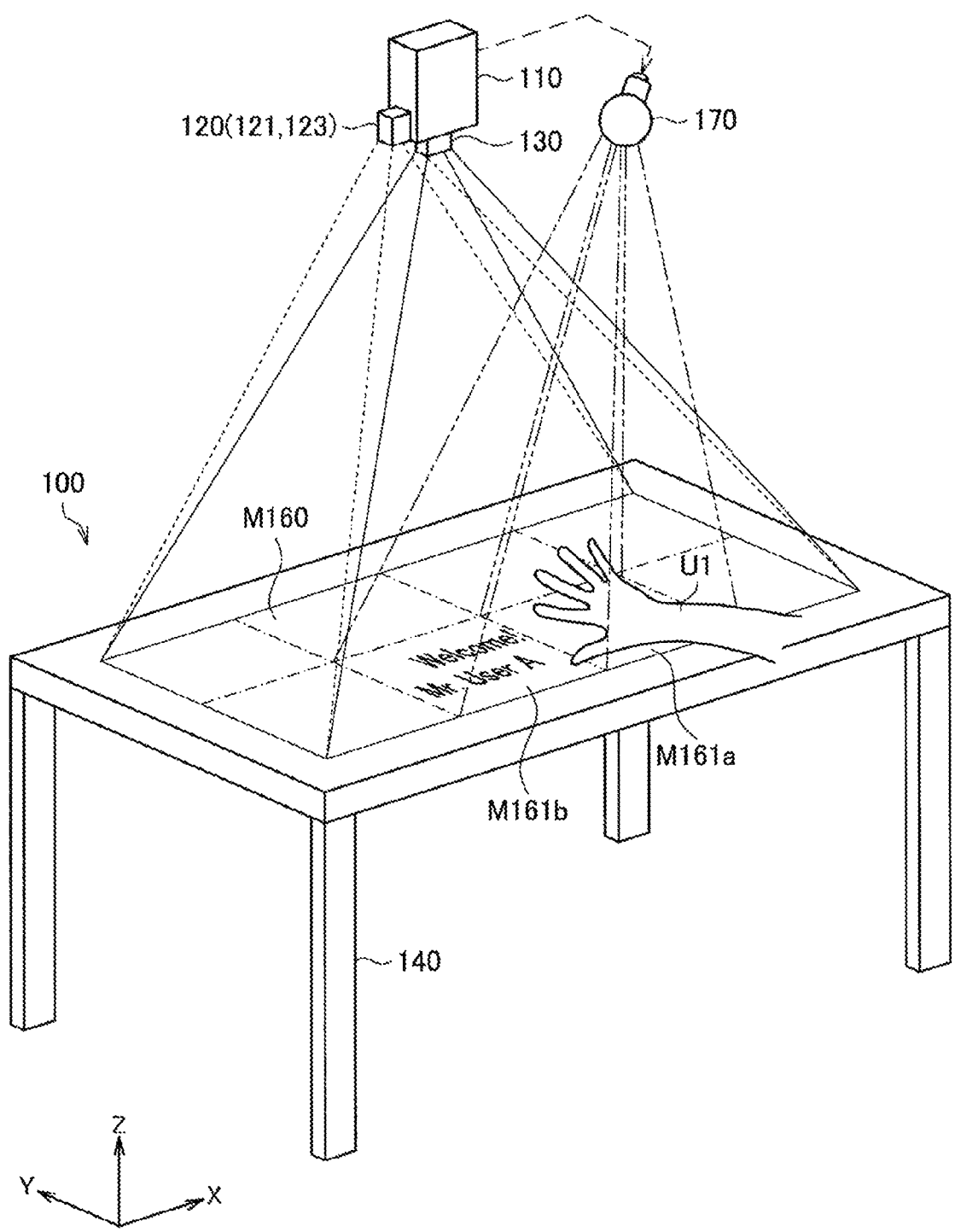
FIG. 14 is an explanatory diagram for describing an example of a schematic configuration of an apparatus according to a third embodiment of the present disclosure.

A description will be given first of an example of a schematic configuration of an apparatus to which a technique according to the third embodiment of the present disclosure is applied with reference to FIG. 14. FIG. 14 is an explanatory diagram for describing an example of a schematic configuration of an apparatus according to the present embodiment and depicts an example of a configuration of a display apparatus for presenting information by projecting video onto a given projection plane. It should be noted that we assume that reference signs in FIG. 14 similar to those in FIG. 1 represent similar targets to those in FIG. 1.

As is understood from comparison between FIG. 14 and FIG. 1, the display apparatus 100 illustrated in FIG. 14 differs from the display apparatus 100 illustrated in FIG. 1 in that a light source 170 is included. Accordingly, a description will be given in this paragraph with primary emphasis on the configuration of the light source 170 and portions associated with control over the light source 170, and the detailed description of other portions (i.e., portions substantially similar to those of the display apparatus 100 illustrated in FIG. 1) will be omitted.

The light source 170 is configured as what is generally called an active light source. Specifically, the light source 170 can irradiate light on the region M160 whose multi-spectral image is to be captured and can control the wavelength of light to be irradiated for each portion of the region M160 (in other words, for each partial region into which the region M160 has been divided). Such a configuration makes it possible to irradiate light in different wavelength bands to a partial region M161a where a user's hand U1 is located and to a partial region M161b, a region other than the partial region M161a onto which display information is projected. As a specific example, the light source 170 may be controlled such that light in a wavelength band that facilitates the detection of feature values appropriate to the spectral properties of the skin pigments is irradiated on the partial region M161a where the user's hand U1 exists (i.e., partial region from which the skin region is detected). Also, the light source 170 may be controlled such that light in a wavelength band that provides improved visibility of display information is irradiated on the partial region M161b onto which the display information in question is projected.

It should be noted that the constituent element corresponding to the control section that controls the actions of the light source 170 may be provided, for example, in the main body 110. Also, the output section 130 that projects video onto the region M160 may play the role of the light source 170. In this case, the output section 130 may control the wavelength band of light to be irradiated on each partial region by controlling video projected onto the region M160 for each partial region into which the region M160 in question has been divided.

An example of a schematic configuration of the apparatus to which the technique according to the third embodiment of the present disclosure is applied has been described with reference to FIG. 14.

<3.4.2. Functional Configuration>

Figure 15:
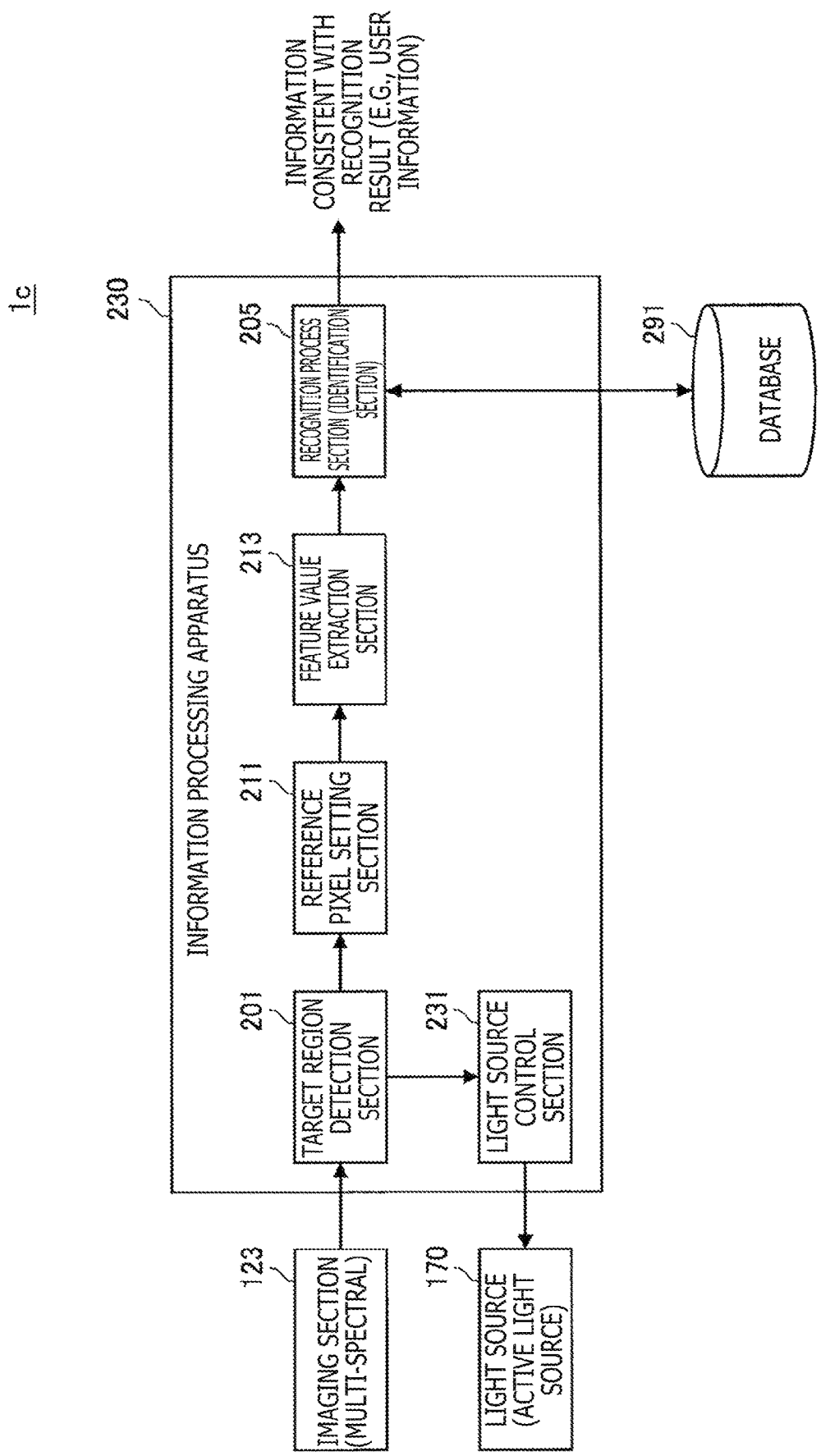
FIG. 15 is a block diagram illustrating an example of a functional configuration of an information processing system according to the third embodiment.

A description will be given next of an example of a functional configuration of the information processing system according to the third embodiment of the present disclosure with reference to FIG. 15. FIG. 15 is a block diagram illustrating an example of a functional configuration of the information processing system according to the present embodiment. It should be noted that, in the description given hereinafter, the information processing system illustrated in FIG. 15 may be referred to as an "information processing system 1c" for distinction from the information processing systems according to the other embodiments described earlier. Also, in a case where no distinction is made therebetween, the information processing system may be simply referred to as the "information processing system 1."

As illustrated in FIG. 15, the information processing system 1c includes the imaging section 123, an information processing apparatus 230, the database 291, and the light source 170. Also, the information processing apparatus 230 includes the target region detection section 201, the reference pixel setting section 211, the feature value extraction section 213, and the recognition process section 205. It should be noted that the imaging section 123, the database 291, the target region detection section 201, the reference pixel setting section 211, the feature value extraction section 213, and the recognition process section 205 are substantially similar to the imaging section 123, the database 291, the target region detection section 201, the reference pixel setting section 211, the feature value extraction section 213, and the recognition process section 205 illustrated in FIG. 9, respectively, and accordingly, a detailed description thereof will be omitted. Also, the light source 170 corresponds to the light source 170 illustrated in FIG. 14.

A light source control section 231 controls the actions of the light source 170, thus controlling the wavelength band of light irradiated from the light source 170 in question. At this time, the light source control section 231 may control the wavelength band of light irradiated from the light source 170 for each partial region on which light is irradiated from the light source 170. As a specific example, the light source control section 231 may acquire information regarding a detection result of a target region (e.g., skin region) from the target region detection section 201 and control the actions of the light source 170 and control the wavelength band of light irradiated on the target region in question such that a feature value can be extracted with more ease from the target region in question. More specifically, the light source control section 231 may control the wavelength band of light irradiated on the target region in question in accordance with the spectral property of the pigment used for extraction of a feature value from the target region in question.

It should be noted that although, in the example illustrated in FIG. 15, the light source 170 and the light source control section 231 have been added to the information processing system 1a depicted in FIG. 9, the functional configuration of the information processing system according to the present embodiment is not necessarily limited to the example illustrated in FIG. 15. For example, the information processing system 1 according to the present embodiment may be configured by adding the light source 170 and the light source control section 231 to the information processing system illustrated in FIG. 2 or FIG. 11 as depicted in FIG. 15.

An example of a functional configuration of the information processing system according to the third embodiment of the present disclosure has been described above with reference to FIG. 15.

<3.4.3. Example of Controlling Light Irradiated from Light Source>

A more detailed description will be given next of an example of controlling light irradiated from the light source 170.

Spectroscopic data acquired by a multi-spectral camera (in other words, multi-spectral image) is determined by the multiplication of the spectral distribution E of light irradiated from the light source, the spectral reflectance S of the subject, and the spectral sensitivity property Q of the multi-spectral camera in question as described on the basis of (Expression 8). Accordingly, in order to acquire spectral data corresponding to a more useful wavelength at the time of extraction of a feature value appropriate to the spectral property of a given pigment from the multi-spectral image, the spectral distribution E of light irradiated from the light source desirably includes the component of the wavelength in question.

As a specific example, we assume that information (feature) useful for extraction of a feature value exists in the vicinity of the wavelength $\lambda_i$ and that a spectral sensitivity $Q_k(\lambda_i)$ of the multi-spectral camera at a wavelength $\lambda_i$ is also sufficient. Meanwhile, in a case where the spectral distribution E of light irradiated from the light source at the wavelength $\lambda_i$ is 0, no spectral component at the wavelength $\lambda_i$ is included in spectral data $R_k$ acquired from the multi-spectral camera.

Accordingly, in a case where a wavelength useful for extraction of a feature value is known, a light source including the component of the wavelength in question is desirably used for the spectral distribution E of light irradiated. Meanwhile, in a case where a wavelength useful for extraction of a feature value has yet to be identified, a light source including components of all possible wavelength bands for the spectral distribution E of light irradiated (ideally, components of all wavelength bands) is preferably used.

An example of controlling light irradiated from the light source 170 has been described above in more detail.

4. Hardware Configuration

Figure 16:
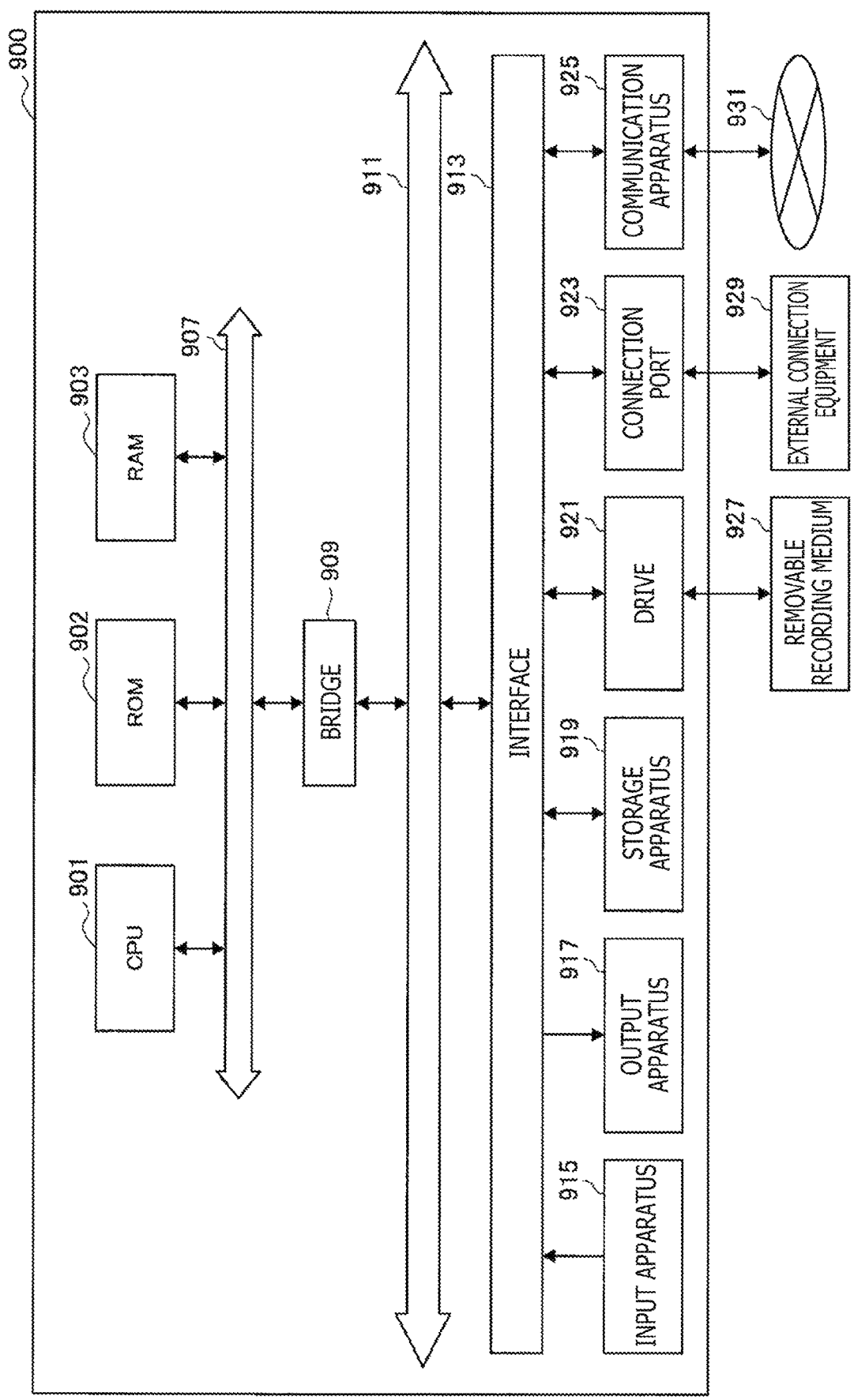
FIG. 16 is a functional block diagram illustrating a configuration example of a hardware configuration of an information processing apparatus included in an information processing system according to an embodiment of the present disclosure.

A detailed description will be given next, with reference to FIG. 16, of an example of a hardware configuration of an information processing apparatus (e.g., information processing apparatus 200 illustrated in FIG. 2) for performing various processing tasks in the information processing system according to an embodiment of the present disclosure. FIG. 16 is a functional block diagram illustrating a configuration example of a hardware configuration of an information processing apparatus included in an information processing system according to an embodiment of the present disclosure.

An information processing apparatus 900 included in the information processing system according to the present embodiment mainly includes a CPU 901, a ROM (Read Only Memory) 903, and a RAM (Random Access Memory) 905. Also, the information processing apparatus 900 further includes a host bus 907, a bridge 909, an external bus 911, an interface 913, an input apparatus 915, an output apparatus 917, a storage apparatus 919, a drive 921, a connection port 923, and a communication apparatus 925.

The CPU 901 functions as an arithmetic processing apparatus and a control apparatus and controls all or some of the actions of the information processing apparatus 900 in accordance with various programs recorded in the ROM 902, the RAM 903, the storage apparatus 919, or a removable recording medium 927. The ROM 902 stores programs, computational parameters, and the like used by the CPU 901. The RAM 903 primarily stores programs, parameters that change as appropriate as a result of execution of the programs, and the like used by the CPU 901. These are connected to each other by the host bus 907 that includes an internal bus such as CPU bus. It should be noted that the target region detection section 201, the feature value extraction section 203, and the recognition process section 205 can be realized by the CPU 901.

The host bus 907 is connected to the external bus 911 such as a PCI (Peripheral Component Interconnect/Interface) bus via the bridge 909. Also, the input apparatus 915, the output apparatus 917, the storage apparatus 919, the drive 921, the connection port 923, and the communication apparatus 925 are connected to the external bus 911 via the interface 913.

The input apparatus 915 is, for example, operating means operated by a user such as a mouse, a keyboard, a touch screen, a button, a switch, a lever, or a pedal. Also, the input apparatus 915 may be, for example, remote-controlling means (what is generally called a remote controller) using infrared radiation or other radio waves, an external connection equipment 929 such as a mobile phone or a PDA that supports operations of the information processing apparatus 900. Further, the input apparatus 915 includes, for example, an input control circuit and the like that generates an input signal on the basis of information input by the user with the above operating means and outputs the information to the CPU 901. The user of the information processing apparatus 900 can input a variety of data or give instructions for processing operations to the information processing apparatus 900 by operating the input apparatus 915.

The output apparatus 917 includes an apparatus capable of notifying the user of acquired information in a visual or aural manner. Among examples of such an apparatus are a liquid crystal display apparatus, an organic EL (Electro Luminescent) display apparatus, a CRT (Cathode Ray Tube) display apparatus, a plasma display apparatus, a display apparatus such as a lamp, an audio output apparatus such as a speaker or a headphone, and a printer apparatus. The output apparatus 917 outputs, for example, results of a variety of processes performed by the information processing apparatus 900. Specifically, the display apparatus displays results of various processes performed by the information processing apparatus 900 in the form of text or image. Meanwhile, the audio output apparatus converts an audio signal including reproduced audio data, acoustic data, and the like into an analog signal and outputs the analog signal.

The storage apparatus 919 is a data storage apparatus configured as an example of a storage section of the information processing apparatus 900. The storage apparatus 919 includes, for example, a magnetic storage section device, a semiconductor storage device, an optical storage device, or a magneto-optical storage device such as an HDD (Hard Disk Drive). The storage apparatus 919 stores programs to be executed by the CPU 901, various data, and the like. It should be noted that the database 291 illustrated in FIG. 2 can be realized by at least any one of the ROM 903, the storage apparatus 919, and the removable recording medium 927. Also, the database 291 in question may be realized by two or more of the ROM 903, the storage apparatus 919, and the removable recording medium 927 used in combination.

The drive 921 is a reader/writer for reading from and writing to a recording medium and is incorporated in the information processing apparatus 900 or attached externally thereto. The drive 921 reads out information recorded in the removable recording medium 927 inserted therein such as a magnetic disk, an optical disc, a magneto-optical disk, or a semiconductor memory, and outputs the information to the RAM 903. Also, the drive 921 can write a record to the removable recording medium 927 inserted therein such as a magnetic disk, an optical disc, a magneto-optical disk, or a semiconductor memory. The removable recording medium 927 is, for example, a DVD medium, an HD-DVD medium, a Blu-ray (registered trademark) medium, or the like. Also, the removable recording medium 927 may be a Compact-Flash (registered trademark) (CF), a flash memory, an SD memory card (Secure Digital memory card), or the like. Also, the removable recording medium 927 may be, for example, an IC card (Integrated Circuit card) with a non-contact type IC chip, electronic equipment, or the like.

The connection port 923 is a port for direct connection to the information processing apparatus 900. Among examples of the connection port 923 are a USB (Universal Serial Bus) port, an IEEE 1394 port, and a SCSI (Small Computer System Interface) port. Among other examples of the connection port 923 are an RS-232C port, an optical audio terminal, and an HDMI (registered trademark) (High-Definition Multimedia Interface) port. If the external connection equipment 929 is connected to the connection port 923, the information processing apparatus 900 acquires a variety of data directly from the external connection equipment 929 or supplies a variety of data to the external connection equipment 929.

The communication apparatus 925 is, for example, a communication interface that includes a communication device or the like used for connection to a communication network 931. The communication apparatus 925 is a communication card for a wired or wireless LAN (Local Area Network), Bluetooth (registered trademark), or a WUSB (Wireless USB), or the like. Also, the communication apparatus 925 may be an optical communication router, a router for ADSL (Asymmetric Digital Subscriber Line), or one of modems for various types of communication. This communication apparatus 925 can, for example, send and receive signals to and from the Internet or other pieces of communication equipment in accordance with a given protocol such as a TCP/IP. Also, the communication network 931 connected to the communication apparatus 925 may include a network or the like connected in a wired or wireless manner and be, for example, the Internet, a home LAN, infrared communication, radio wave communication, satellite communication, or the like.

An example of a hardware configuration has been demonstrated above that can realize the functions of the information processing apparatus 900 included in the information processing system according to an embodiment of the present disclosure. Each of the above constituent elements may include a general-purpose member or hardware specifically designed to achieve the function of each of the constituent element. Accordingly, it is possible to change the hardware configuration to use as appropriate in accordance with the technical level at the time of carrying out the present embodiment. It should be noted that, although not illustrated in FIG. 16, various constituent elements corresponding to the information processing apparatus 900 included in the information processing system are naturally provided.

It should be noted that a computer program for realizing the functions of the information processing apparatus 900 included in the information processing system according to the present embodiment as described above can be created and implemented in a personal computer or the like. Also, it is possible to provide a computer-readable recording medium storing such a computer program. The recording medium is, for example, a magnetic disk, an optical disc, a magneto-optical disk, a flash memory, or the like. Also, the above computer program may be, for example, delivered via a network without using any recording medium. Also, the number of computers used to execute the computer program is not specifically limited. For example, the computer program in question may be executed in cooperation between a plurality of computers (e.g., a plurality of servers).

5. Conclusion

As described above, in an information processing system according to an embodiment of the present disclosure, an information processing apparatus includes an acquisition section and an extraction section. The acquisition section acquires a multi-spectral image. The extraction section extracts a feature value from the multi-spectral image in question. Specifically, the acquisition section acquires a multi-spectral image consistent with an imaging result of a subject by using light divided into a plurality of wavelength bands. Also, the extraction section extracts a feature value by carrying out a computational process (e.g., weighting process) on the basis of a weighting coefficient appropriate to the absorption spectral properties of one or more pigments.

The configuration as described above suppresses the impact of some pigments (e.g., pigments whose impact that manifests itself depending on the circumstances is likely to change) among a plurality of pigments included in a given subject, thus allowing for extraction, as a feature value, of information inherent to the subject in question that offers higher robustness to the change in circumstances. In other words, by extracting information inherent to a subject as a feature value on the basis of the configuration as described above, it is possible, irrespective of the change in circumstances at the time, to expect an advantageous effect of ensuring identity of the feature value in question. That is, the information processing system according an embodiment of the present disclosure can extract information inherent to a subject from a captured image in a more suitable manner, irrespective of the change in circumstances at the time of image (multi-spectral image) capture.

Also, by using the feature value as described above, for example, for identification or authentication of a given target (e.g., user), it is possible to realize identification or authentication that offers higher robustness to the change in circumstances at the time and higher accuracy.

In particular, by using the technique according to the present disclosure for personal identification or authentication using at least a body region of a user, it is possible to realize personal identification or authentication with higher accuracy without involving a troublesome operation even in a case where a body region such as hand that readily changes its shape is used for identification or authentication. Also, even in the case where the state changes from one moment to another due to sunburn or the like (in particular, appearance such as a color), it is possible to realize personal identification or authentication that offers higher robustness to the change in the state in question by using the technique according to the present disclosure. Also, the use of the technique according to the present disclosure allows for speedy user identification or authentication without involving a troublesome operation, thus making it possible to present information consistent with the result of the identification or the authentication in question with a shorter delay (in other words, to present the information in question in a timely manner). Also, by using the technique according to the present disclosure, it is possible to carry out personal identification or authentication in a stable and highly accurate manner even under the circumstances where, for example, part of the target body region is covered with another object or the like and, therefore, only part of the body region in question is exposed.

It should be noted that although the above description has been given with primary emphasis on an example of extracting a feature value in accordance with the spectral property of a skin pigment from a captured image (multi-spectral image) of a user's skin as a subject, the example does not necessarily limit the target of application of the technique according to the present disclosure. That is, as long as the type of pigment whose impact manifests itself during image capture and the spectral property of the pigment in question are known, it is possible to extract information inherent to the subject of the captured image in question as a feature value. Also, although the above description has been given with emphasis on an example of using an extracted feature value for identification or authentication of a given target (e.g., user), the use of the feature value in question is not specifically limited, and it is possible to use the feature value, for example, for determining a degree of deterioration of a given target.

As a specific example, a multi-layer is formed by multi-layer coating, special paints, or the like in automobiles, ships, aircrafts, and the like. It is possible to use a feature value extracted on the basis of the technique according to the present disclosure for analyzing the state of such a multi-layer film (e.g., analyzing the degree of deterioration). Also, it is possible to use a feature value extracted on the basis of the technique according to the present disclosure for identifying a solid (e.g., automobile, ship, aircraft, and the like) having the multi-layer film in question from a captured image of the multi-layer film in question as a subject.

Also, in pharmaceuticals as well, there are cases where tablet coatings, gel capsules, and the like are formed as multi-layer films, and it is possible to use a feature value extracted on the basis of the technique according to the present disclosure for analyzing the multi-layer films in question and identifying pharmaceutical solids in these cases.

Also, many of functional films (i.e., insulating, adhesive, sticky, antiseptic, phase-difference, polarizing, AR, and so on) applied to electronic parts and the like look transparent to detection by three human complexes (i.e., are difficult to view). Even in such a case, it is possible to grasp the state of the functional film in question, identify the individual functional film in question, and perform other tasks by using a feature value extracted on the basis of the technique according to the present disclosure from a captured image of the multi-layer film in question as a subject. Also, it is possible to apply the technique according to the present disclosure for acquiring information of a solid from the state of an oxide film, a nitride film, resist, DLC (Diamond-Like Carbon) coating, an organic film, a sealing agent, an anti-corrosive agent, an anti-fog agent, or the like in a semiconductor package.

Although the preferred embodiments of the present disclosure have been described in detail above with reference to the attached drawings, the present disclosure is not limited in technical scope to these examples. It is apparent that a person having ordinary knowledge in the technical field of the present disclosure can arrive at various alteration or modification examples without departing from the technical concept described in the claims, and these are also naturally construed as falling within the technical scope of the present disclosure.

Also, the advantageous effects described in the present specification are merely descriptive or illustrative and are not restrictive. That is, the technique according to the present disclosure can provide other advantageous effects apparent to a person skilled in the art from the description of the present specification together with or in place of the above advantageous effect.

It should be noted that the following configurations also fall within the technical scope of the present disclosure.

(1)

An information processing apparatus including:

an acquisition section adapted to acquire a multi-spectral image consistent with an imaging result of a subject by using light divided into a plurality of wavelength bands; and an extraction section adapted to extract a feature value by carrying out a computational process, on the multi-spectral image, on the basis of coefficients appropriate to absorption spectral properties of one or more pigments.

(2)

The information processing apparatus according to (1), in which the one or more pigments include at least partially one or more skin pigments.

(3)

The information processing apparatus according to (2), in which the extraction section extracts the feature value by performing a weighting process appropriate to an absorption spectral property of at least melanin on the multi-spectral image as the computational process.

(4)

The information processing apparatus according to (3) in which the extraction section extracts the feature value by performing the weighting process appropriate to absorption spectral properties of at least the melanin and hemoglobin on the multi-spectral image.

(5)

The information processing apparatus according to (4), in which the extraction section extracts the feature value by performing the weighting process on the multi-spectral image separately for oxidized hemoglobin and deoxidized hemoglobin as the hemoglobin.

(6)

The information processing apparatus according to (5), in which the plurality of wavelength bands includes six wavelength bands whose respective center wavelengths are generally equal to 425 nm, 510 nm, 570 nm, 760 nm, 870 nm, and 970 nm.

(7)

The information processing apparatus according to any one of (1) to (6), in which the extraction section calculates the feature value by suppressing an impact of at least some of the one or more pigments that have manifested itself in the multi-spectral image on the basis of the coefficients appropriate to the absorption spectral properties of the one or more pigments in question.

(8)

The information processing apparatus according to (7), in which the computational process includes a weighting process based on an absorbance at a first wavelength and an absorbance at a second wavelength different from the first wavelength appropriate to absorption spectral properties of at least some of the one or more pigments at a spatial position corresponding to at least a region of the multi-spectral image, and the extraction section extracts the feature value by suppressing the impact of the pigments in question that has manifested itself in the region in question through the weighting process.

(9)

The information processing apparatus according to (7), in which in a case where N is an integer equal to or greater than 1, the computational process includes a weighting process based on an absorbance at each of N or more different wavelengths appropriate to absorption spectral properties of N types of pigments at a spatial position corresponding to at least a region of the multi-spectral image, and the extraction section extracts the feature value by suppressing the impact of some of the N types of pigments that has manifested itself in the region in question through the weighting process.

(10)

The information processing apparatus according to (7), in which the computational process includes a weighting process based on a variation in absorbance appropriate to absorption spectral properties of at least some of the one or more pigments at a spatial position corresponding to at least a region of the multi-spectral image, and the extraction section extracts the feature value by extracting an impact attributable to the some pigments in question that has manifested itself in the region in question through the weighting process.

(11)

The information processing apparatus according to any one of (1) to (6), in which the extraction section extracts, through the computational process based on an absorbance at a wavelength appropriate to absorption spectral properties of at least some of the one or more pigments at a spatial position corresponding to at least a region of the multi-spectral image, the feature value by extracting an impact attributable to the some pigments in question that has manifested itself in the region in question.

(12)

The information processing apparatus according to any one of (1) to (6), in which the computational process includes a weighting process based on the coefficients appropriate to a variation of absorbance in a time direction appropriate to absorption spectral properties of at least some of the one or more pigments for the multi-spectral image, and the extraction section extracts the feature value through the weighting process.

(13)

The information processing apparatus according to any one of (1) to (12), in which the extraction section extracts the feature value corresponding to at least a region of the multi-spectral image as data having the feature value arranged two-dimensionally for each of portions of the region in question.

(14)

The information processing apparatus according to (13), in which by defining part of the region as a reference point and setting the feature value corresponding to each portion of the region in question as a difference from the feature value at the reference point in question, the extraction section extracts the feature value corresponding to the region in question.

(15)

The information processing apparatus according to any one of (1) to (14) including:

an identification section adapted to identify an individual on the basis of the feature value extracted from the multi-spectral image and the feature value registered in advance as personal data.

(16)

The information processing apparatus according to any one of (1) to (15) including:

a detection section adapted to detect a skin region from the multi-spectral image; and a control section adapted to control, for each partial region into which a real space region corresponding to an image capture range of the multi-spectral image has been divided, a wavelength band of light to be irradiated on the partial region from a light source, in which
the control section performs control such that light in a wavelength band appropriate to absorption spectral properties of at least some of the one or more pigments is irradiated on the partial region corresponding to the detected skin region.

(17)
An information processing method by a computer including:
acquiring a multi-spectral image consistent with an imaging result of a subject by using light divided into a plurality of wavelength bands; and
extracting a feature value by carrying out a computational process on the multi-spectral image on the basis of coefficients appropriate to absorption spectral properties of one or more pigments.

(18)
A program causing a computer to execute:
acquiring a multi-spectral image consistent with an imaging result of a subject by using light divided into a plurality of wavelength bands; and
extracting a feature value by carrying out a computational process on the multi-spectral image on the basis of coefficients appropriate to absorption spectral properties of one or more pigments.

REFERENCE SIGNS LIST

1 Information processing system
100 Display apparatus
110 Main body
120 Sensor box
121 Detection section
123 Imaging section
130 Output section
170 Light source
200, 210, 220, 230 Information processing apparatus
201 Target region detection section
203 Feature value extraction section
2031 Block division section
2033 Computation section
205 Recognition process section
211 Reference pixel setting section
213 Feature value extraction section
221 Motion region tracking section
223 Feature value extraction section
231 Light source control section
291 Database
293 Past image storage section

The invention claimed is:

1. An information processing apparatus, comprising:
a central processing unit (CPU) configured to:
acquire a multi-spectral image consistent with an imaging result of a subject by using light divided into a plurality of wavelength bands; and
extract a feature value by carrying out a computational process on the multi-spectral image based on coefficients appropriate to absorption spectral properties of a plurality of pigments, wherein
the plurality of pigments includes at least partially one or more skin pigments,
the feature value is extracted by a first weighting process and a second weighting process on the multi-spectral image as the computational process,
the first weighting process is performed based on a weighting coefficient determined from, of absorption spectra of the plurality of pigments, a ratio between a first absorption coefficient of hemoglobin at a first wavelength and a second absorption coefficient of hemoglobin at a second wavelength, and
the second weighting process is based on the coefficients appropriate to a variation of absorbance in a time direction appropriate to absorption spectral properties of some of the plurality of pigments for the multi-spectral image.

2. The information processing apparatus according to claim 1, wherein
the CPU is further configured to extract the feature value by the first weighting process appropriate to absorption spectral properties of at least melanin and hemoglobin on the multi-spectral image.

3. The information processing apparatus according to claim 2, wherein
the CPU is further configured to extract the feature value by the first weighting process on the multi-spectral image separately for oxidized hemoglobin and deoxidized hemoglobin as the hemoglobin.

4. The information processing apparatus according to claim 3, wherein
the plurality of wavelength bands includes six wavelength bands whose respective center wavelengths are equal to 425 nm, 510 nm, 570 nm, 760 nm, 870 nm, and 970 nm.

5. The information processing apparatus according to claim 1, wherein
the CPU is further configured to calculate the feature value by suppressing an impact of at least some of the plurality of pigments that have manifested itself in the multi-spectral image based on the coefficients appropriate to the absorption spectral properties of the plurality of pigments.

6. The information processing apparatus according to claim 5, wherein
the computational process includes a third weighting process based on an absorbance at a first wavelength and an absorbance at a second wavelength different from the first wavelength appropriate to absorption spectral properties of the at least some of the plurality of pigments at a spatial position corresponding to at least a region of the multi-spectral image, and
the feature value is extracted by suppressing the impact of the at least some of the plurality of pigments that has manifested itself in the region through the third weighting process.

7. The information processing apparatus according to claim 5, wherein
in a case where N is an integer equal to or greater than 1, the computational process includes a third weighting process based on an absorbance at each of N or more different wavelengths appropriate to absorption spectral properties of N types of pigments at a spatial position corresponding to at least a region of the multi-spectral image, and
the feature value is extracted by suppressing the impact of some of the N types of pigments that has manifested itself in the region through the third weighting process.

8. The information processing apparatus according to claim 5,
the computational process includes a third weighting process based on a variation in absorbance appropriate to absorption spectral properties of the at least some of the plurality of pigments at a spatial position corresponding to at least a region of the multi-spectral image, and the feature value is extracted by extracting an impact attributable to the least some of the plurality of pigments that has manifested itself in the region through the third weighting process.

9. The information processing apparatus according to claim 1, wherein the feature value is extracted, through the computational process based on an absorbance at a wavelength appropriate to absorption spectral properties of at least some of the plurality of pigments at a spatial position corresponding to at least a region of the multi-spectral image, by extracting an impact attributable to the at least some of the plurality of pigments that has manifested itself in the region.

10. The information processing apparatus according to claim 1, wherein the CPU is further configured to extract the feature value corresponding to at least a region of the multi-spectral image as data having the feature value arranged two-dimensionally for each of portions of the region.

11. The information processing apparatus according to claim 10, wherein the CPU is further configured to extract, by defining a part of the region as a reference point and setting the feature value corresponding to each portion of the region as a difference from the feature value at the reference point, the feature value corresponding to the region.

12. The information processing apparatus according to claim 1, wherein the CPU is further configured to identify an individual based on the feature value extracted from the multi-spectral image and the feature value registered in advance as personal data.

13. The information processing apparatus according to claim 1, wherein the CPU is further configured to:

detect a skin region from the multi-spectral image; and control, for each partial region into which a real space region corresponding to an image capture range of the multi-spectral image has been divided, a wavelength band of light to be irradiated on a partial region from a light source, wherein control such that the light in the wavelength band appropriate to absorption spectral properties of at least some of the plurality of pigments is irradiated on the partial region corresponding to the detected skin region.

14. An information processing method, comprising:

acquiring a multi-spectral image consistent with an imaging result of a subject by using light divided into a plurality of wavelength bands; and extracting a feature value by carrying out a computational process on the multi-spectral image based on coefficients appropriate to absorption spectral properties of a plurality of pigments, wherein the plurality of pigments includes at least partially one or more skin pigments, the feature value is extracted by a first weighting process and a second weighting process on the multi-spectral image as the computational process, the first weighting process is performed based on a weighting coefficient determined from, of absorption spectra of the plurality of pigments, a ratio between a first absorption coefficient of hemoglobin at a first wavelength and a second absorption coefficient of hemoglobin at a second wavelength, and the second weighting process is based on the coefficients appropriate to a variation of absorbance in a time direction appropriate to absorption spectral properties of some of the plurality of pigments for the multi-spectral image.

15. A non-transitory computer-readable medium having stored thereon computer-executable instructions which, when executed by a computer, cause the computer to execute operations, the operations comprising:

acquiring a multi-spectral image consistent with an imaging result of a subject by using light divided into a plurality of wavelength bands; and extracting a feature value by carrying out a computational process on the multi-spectral image based on coefficients appropriate to absorption spectral properties of a plurality of pigments, wherein the plurality of pigments includes at least partially one or more skin pigments, the feature value is extracted by a first weighting process and a second weighting process on the multi-spectral image as the computational process, the first weighting process is performed based on a weighting coefficient determined from, of absorption spectra of the plurality of pigments, a ratio between a first absorption coefficient of hemoglobin at a first wavelength and a second absorption coefficient of hemoglobin at a second wavelength, and the second weighting process is based on the coefficients appropriate to a variation of absorbance in a time direction appropriate to absorption spectral properties of some of the plurality of pigments for the multi-spectral image.

\* \* \* \* \*